US012180461B2

(12) United States Patent
Chalker et al.

(10) Patent No.: US 12,180,461 B2
(45) Date of Patent: Dec. 31, 2024

(54) CHARCOAL-FREE CULTURE MEDIA FOR LEGIONELLA

(71) Applicant: SECRETARY OF STATE FOR HEALTH AND SOCIAL CARE, London (GB)

(72) Inventors: Victoria Jane Chalker, London (GB); Owen Brad Spiller, Cardiff (GB); Edward Portal, Cardiff (GB)

(73) Assignee: Secretary of State for Health and Social Care, London (GB)

( * ) Notice: Subject to any disclaimer, the term of this patent is extended or adjusted under 35 U.S.C. 154(b) by 983 days.

(21) Appl. No.: 17/270,620

(22) PCT Filed: Aug. 23, 2019

(86) PCT No.: PCT/GB2019/052382
§ 371 (c)(1),
(2) Date: Feb. 23, 2021

(87) PCT Pub. No.: WO2020/039213
PCT Pub. Date: Feb. 27, 2020

(65) Prior Publication Data

US 2021/0222118 A1 Jul. 22, 2021

(30) Foreign Application Priority Data

Aug. 24, 2018 (GB) ..................................... 1813884

(51) Int. Cl.

| | |
|---|---|
| *C12N 1/20* | (2006.01) |
| *A61K 9/00* | (2006.01) |
| *A61K 33/14* | (2006.01) |
| *A61P 31/04* | (2006.01) |
| *C12Q 1/18* | (2006.01) |

(52) U.S. Cl.
CPC .............. *C12N 1/20* (2013.01); *A61K 9/0078* (2013.01); *A61K 33/14* (2013.01); *A61P 31/04* (2018.01); *C12Q 1/18* (2013.01)

(58) Field of Classification Search
None
See application file for complete search history.

(56) References Cited

U.S. PATENT DOCUMENTS 8,709,746 B2 4/2014 Cellier et al.

FOREIGN PATENT DOCUMENTS

JP H10-309189 A 11/1998
WO 2010043818 A1 4/2010

OTHER PUBLICATIONS

Jayme et al. Nature vol. 334 Aug. 11, 1988 547-548.*
Armon, R. and P. Payment, "A transparent medium for isolation of Legionella pneumophia from environmental water sources," Elsevier: Journal of Microbiological Methods 11(1): 65-71, 1990.
De Giglio, O., et al., "Antibiotic susceptibility of Legionella pneumophila strains isolated from hospital water systems in Southern Italy," Elsevier: Environmental Research 142: 586-590, 2015.
International Search Report and Written Opinion mailed Dec. 13, 2019, issued in corresponding Application No. PCT/GB2019/052382, filed Aug. 23, 2019, 20 pages.
International Preliminary Report on Patentability mailed Nov. 27, 2020, issued in corresponding Application No. PCT/GB2019/052382, filed Aug. 23, 2019, 20 pages.
Second Written Opinion mailed Sep. 8, 2020, issued in corresponding Application No. PCT/GB2019/052382, filed Aug. 23, 2019, 6 pages.
Search Report mailed Jan. 31, 2019, issued in corresponding Application No. GB1813884.2, filed Aug. 24, 2018, 5 pages.
Pan, M.J & Van Staden, J.; "The Use of Charcoal in In Vitro Culture—A review," Plant Growth Regulation 26:155-163, 1998.
Jenkins, M.A., "Serum Protein Electrophoresis," In: Palfrey S.M. 35 (eds) Clinical Applications of Capillary Electrophoresis, Methods in Molecular Medicine, vol. 27, Humana Press, Totowa, NJ, 1999.
Feeley, J.C., et al., "Charcoal-Yeast Extract Agar: Primary Isolation Medium for Legionella pneumophila," Journal of Clinical Microbiology 10(4):437-441, Oct. 1979.
Pasculle, A.W., et al., "Pittsburgh Pneumonia Agent: Direct Isolation from Human Lung Tissue," The Journal of Infectious Diseases 141(6):727-732, Jun. 1980.
Vandewalle-Capo, M., et al., Minimum Inhibitory Concentration (MIC) Distribution Among Wild-Type Strains of Legionella pneumophila Identifies a Subpopulation With Reduced Susceptibility to Macrolides Owing to Efflux Pump Genes, International Journal of Antimicrobial Agents 50:684-689, 2017.
Wilson, R.E., et al., "Antibiotic Susceptibility of Legionella pneumophila Strains Isolated in England and Wales 2007-17," Journal of Antimicrobial Chemotherapy 73:2757-2761, 2018.

* cited by examiner

*Primary Examiner* — Oluwatosin A Ogunbiyi
(74) *Attorney, Agent, or Firm* — Christensen O'Connor Johnson Kindness PLLC

(57) ABSTRACT

The present invention provides in vitro methods for culturing *Legionella*, comprising incubating a *Legionella* bacterium on a charcoal-free solid agar medium comprising: serum, wherein the serum is present at a concentration of 1%-35% (v/v); a nitrogen source; and an iron source. Charcoal-free solid agar media for use in methods of the invention are also provided.

20 Claims, 2 Drawing Sheets

CHARCOAL-FREE CULTURE MEDIA FOR LEGIONELLA

The present invention relates to a method for culturing bacteria, for example on solid media which is suitable for screening antibiotics, and use of an alkaline earth metal and/or alkali metal for suppressing bacteria.

The genus *Legionella* is a pathogenic group of Gram-negative bacteria that includes the species *L. pneumophila*, infections with which cause "legionellosis" (a collective term which encompasses all diseases caused by *Legionella*). Such diseases include a pneumonia-type illness called Legionnaires' disease and a mild flu-like illness called Pontiac fever. *Legionella* are typically aquatic bacteria, and thrive in areas such as cooling towers, swimming pools, domestic water systems and showers, ice-making machines, refrigerated cabinets, whirlpool spas, hot springs, and fountains.

Culturing *Legionella* (e.g. for the detection of *Legionella*, and/or diagnosis of a subject with a *Legionella*) is perturbed by a lack of suitable culturing methods and means. An associated problem includes the difficulties in screening for new *Legionella* antibiotics and biocidal reagents. This is particularly problematic, as the risk of antibiotic resistance development in *Legionella* represents a significant public health concern, and there is a need to identify new antibiotics. Currently, culturing *Legionella* on plates (e.g. on solid culture medium) currently relies on the use of Buffered Charcoal Yeast Extract (BCYE) agar medium. Whilst the BCYE medium has become the gold standard for isolating and culturing *Legionella*, it suffers from the drawback that charcoal used therein (thought to be necessary to absorb unidentified toxins which otherwise inhibit *Legionella* growth) disadvantageously absorbs antibiotics non-specifically. By absorbing antibiotics in the medium, charcoal prevents the antibiotics from contacting the bacteria to exert toxicity, thus preventing the elucidation of the effect of antibiotics (e.g. candidate antibiotics to be screened) on the growth of *Legionella*.

Previous attempts to culture *Legionella* in the absence of charcoal, however, have relied on using liquid cultures e.g. in Buffered Yeast Extract broth. Such culturing does not allow for the automated, high throughput screening methodologies possible with solid medium (e.g. agar plates) and requires sterilisation of screening equipment after contact with broth. However, the development of further solid culturing methods and means has suffered from a lack of knowledge of medium components (e.g. additives and ingredients) which would not be toxic to the highly sensitive *Legionella* bacteria.

The present invention solves one or more of the above mentioned problems.

The present invention provides a charcoal-free solid agar medium which allows for culturing of *Legionella* on solid medium in the presence of agar-derived toxins, without need for charcoal. Such toxins are believed to be free fatty acids and/or free radicals. No particular treatment of the agar used in the medium is required. For example, washing of agar with water is not required. This is highly advantageous, and avoids the compromised sterility of agar (e.g. autoclaved agar) which may result from washing.

The present invention is predicated on the surprising finding that charcoal may be omitted from an agar-based solid culture medium comprising serum, with the serum allowing *Legionalla* to grow on agar (e.g. in the presence of agar derived toxins). This was highly unexpected, as it was previously believed that charcoal was a necessary component of agar-based culture medium for solid cultures (to absorb undefined toxins which otherwise inhibit growth of *Legionella*). It is for this reason that charcoal is routinely used (e.g. required) in the prior art, despite the fact that it also absorbs antibiotics. A charcoal-free solid agar medium of the present invention advantageously does not (e.g. significantly) perturb the activity of an antibiotic therein. Thus, the charcoal-free solid agar medium is particularly suited for culturing *Legionella* when determining the bacteria's susceptibility to antimicrobials (e.g. during antibiotic screening).

In one aspect the invention provides an in vitro method for culturing *Legionella*, comprising incubating a *Legionella* bacterium on a charcoal-free solid agar medium comprising:

a) serum, wherein the serum is present at a concentration of 1%-35% (v/v);
b) a nitrogen source; and
c) an iron source.

The term "in vitro" encompasses ex vivo culturing of *Legionella*.

Another aspect of the invention provides use of a charcoal-free solid agar medium for culturing *Legionella*, wherein the charcoal-free solid agar medium comprises:

a) serum, wherein the serum is present at a concentration of 1%-35% (v/v);
b) a nitrogen source; and
c) an iron source.

A further aspect of the invention provides a charcoal-free solid agar medium for culturing *Legionella*, comprising:

a) serum, wherein the serum is present at a concentration of 1%-35% (v/v);
b) a nitrogen source; and
c) an iron source.

In a yet further aspect, there is provided a method for manufacturing a charcoal-free solid agar medium for culturing *Legionella*, comprising combining the following components to provide an admixture:

a) an agar solution;
b) serum, to provide a serum concentration of 1%-35% (v/v);
c) a nitrogen source; and
d) an iron source; and allowing the admixture to set to provide a charcoal-free solid agar medium.

The invention embraces a charcoal-free solid agar medium for culturing *Legionella* obtainable by said method for manufacturing.

In another aspect, there is provided a screening method for identifying an antibiotic suitable for suppressing the growth of *Legionella*, comprising:

a) contacting a *Legionella* bacterium with a charcoal-free solid agar medium to provide a test sample, wherein the charcoal-free solid agar medium comprises:
   i. serum, wherein the serum is present at a concentration of 1%-35%;
   ii. a nitrogen source; and
   iii. an iron source;
b) incubating the test sample in the presence of a candidate antibiotic; and
c) identifying said candidate antibiotic as suitable for suppressing the growth of *Legionella* when the bacterial load of said *Legionella* in the test sample subsequent to incubation is lower than a bacterial load of *Legionella* in a control sample, wherein the control sample is incubated in the absence of said candidate antibiotic; or d) identifying said candidate antibiotic as unsuitable for suppressing the growth of *Legionella* when the bacterial load of said *Legionella* in the test sample subsequent to incubation is the same as or greater than the bacterial load of *Legionella* in a control sample, wherein the control sample is incubated in the absence of said candidate antibiotic.

The term "bacterial load" means the population of bacterial cells, and may be measured by determining the density and/or size of a bacterial colony.

Advantageously, the charcoal-free solid agar medium may be used for culturing *Legionella* in the presence of agar-derived toxins. The term "agar-derived toxins" refers to undefined toxins present in agar, typically present in agar following autoclaving. Said toxins inhibit/suppress the growth of *Legionella*, and the prior art media has employed charcoal (e.g. activated charcoal) to absorb agar-derived toxins. Surprisingly the inventors have found that a medium of the present invention can support the growth of *Legionella* on a medium in the presence of such toxins, due to the presence of animal serum in the medium. Said medium does not rely on the presence of charcoal (e.g. activated charcoal) to support growth.

Furthermore the charcoal-free solid agar medium (e.g. media) of the present invention does not require washing of agar (e.g. following autoclaving) to remove such toxins. This advantageously avoids the need for using excessive amounts of water to wash toxins off of the agar, which is environmentally unfriendly.

A charcoal-free solid agar medium of the invention preferably provides a means for culturing *Legionella* in the absence of charcoal. In one embodiment, a charcoal-free solid agar medium of the present invention does not comprise charcoal. In a preferably embodiment, a charcoal-free solid agar medium of the present invention does not comprise activated charcoal.

The term "charcoal" means a form of carbon processed to have small, low-volume pores (e.g. that increase the surface area) which is available for adsorption and/or chemical reactions. Charcoal is a commonly used component of culture media, for example as described in Pan, M. & Staden, J. Plant Growth Regulation (1998) 26: 155 (incorporated herein by reference). The charcoal described herein may be activated charcoal.

The term "charcoal-free" means that the charcoal-free solid agar medium is substantially free from charcoal, such as activated charcoal. In one embodiment, wherein the charcoal-free solid agar medium is substantially free from charcoal, the charcoal-free solid agar medium comprises a charcoal concentration of less than 1% (of the total volume of the solid microbiological culture medium); for example, a concentration less than 0.8%, 0.6%, 0.4%, or 0.2%.

Thus, in one embodiment, the term "substantially free from charcoal" means a charcoal concentration of less than 1% (w/v); for example, a concentration less than 0.8% (w/v), 0.6% (w/v), 0.4% (w/v), or 0.2% (w/v).

In a preferable embodiment, wherein the charcoal-free solid agar medium is substantially free from charcoal, the charcoal-free solid agar medium comprises a charcoal concentration of less than 0.1% (w/v); more preferably a concentration of less than 0.08% (w/v), 0.06% (w/v), 0.04% (w/v) or 0.02% (w/v).

The term "serum" may be used synonymously with the term "serum isolated from blood". Thus, the term a "serum" preferably means the liquid fraction of blood (e.g. whole blood) that is obtained/collected from clotted (e.g. coagulated) blood.

A serum may be obtained from blood by coagulating (e.g. clotting) a blood sample and subsequently separating the serum from the remaining blood components/fractions (e.g. red blood cells), preferably by centrifugation. The blood may be coagulated by incubating the blood for a suitable time at a suitable temperature (e.g. incubating for 20-40 minutes, typically at a temperature of 15-30° C.). Said centrifugation may comprise centrifuging at 1,000-2,000×g for 5-20 minutes (preferably about 10 minutes).

In a preferable embodiment, the term "serum" means a supernatant obtained by centrifuging a coagulated blood sample. Preferably, the serum is an isolated serum sample (isolated from blood).

In a preferable embodiment, the serum is a commercially available animal serum preparation, for example obtainable from ThermoFisher Scientific (e.g. catalogue number 16050130, 16050122, 26050070 and/or 26050088).

In one embodiment, the serum comprises a protein concentration of between 50-100 g/L. For example, the protein concentration may between 55-95 g/L, 60-90 g/L, 65-85 g/L, or 70-80 g/L. Preferably, the serum comprises a protein concentration of between 60-80 g/L The serum may comprise an albumin concentration of between 25-75 g/L. For example, the serum may comprise an albumin concentration of between 30-75 g/L, 35-70 g/L, 35-50 g/L, 40-65 g/L, or 45-60 g/L.

Additionally of alternatively, the serum may comprise a globulin (e.g. α-1 globulin, α-2 globulin and β globulin) concentration of between 15-50 g/L. For example, the serum may comprise a globulin concentration of between 20-45 g/L, 25-40 g/L, 20-35 g/L, or 30-35 g/L.

The serum may comprise:

- an α-1 globulin concentration of 0.5-5 g/L, for example 1-4 g/L, or 1-3 g/L;
- an α-2 globulin concentration of 2-12 g/L, for example 4-10 g/L, 6-10 g/L, or 6-8 g/L; and/or
- a β globulin concentration of 5-15 g/L, for example 7-11 g/L, or 8-10 g/L.

Said serum protein concentrations are preferably the pre-dilution concentrations. The concentrations present in the charcoal-free solid agar medium are diluted by the appropriate factor, depending on the volume of serum present in the solid agar culture medium. For example, where the serum comprises a protein concentration of between 50-100 g/L, and the serum is present in the charcoal-free solid agar medium at a concentration of 10% (v/v): then the serum protein concentration in the charcoal free solid agar medium may be 5-10 g/L. Typical serum protein concentrations in the charcoal free solid agar medium (once formulated) are outlined below.

In one embodiment, the serum comprises a protein concentration of between 5-10 g/L. For example, the protein concentration may between 5.5-9.5 g/L, 6-9 g/L, 6.5-8.5 g/L, or 7-8 g/L. Preferably, the serum comprises a protein concentration of between 6-8 g/L The serum may comprise an albumin concentration of between 2.5-7.5 g/L. For example, the serum may comprise an albumin concentration of between 3-7.5 g/L, 3.5-7 g/L, 3.5-5 g/L, 4-6.5 g/L, or 4.5-6 g/L.

Additionally of alternatively, the serum may comprise a globulin (e.g. α-1 globulin, α-2 globulin and β globulin) concentration of between 1.5-5 g/L. For example, the serum may comprise a globulin concentration of between 2-4.5 g/L, 2.5-4 g/L, 2-3.5 g/L, or 3-3.5 g/L.

The serum may comprise:

- an α-1 globulin concentration of 0.05-0.5 g/L, for example 0.1-0.4 g/L, or 0.1-0.3 g/L;

an α-2 globulin concentration of 0.2-1.2 g/L, for example 0.4-1 g/L, 0.6-1 g/L, or 0.6-0.8 g/L; and/or a β globulin concentration of 0.5-1.5 g/L, for example 0.7-1.1 g/L, or 0.8-1.0 g/L.

Serum protein concentrations may be determined by any suitable method known in the art; for example, by Serum Protein Electrophoresis. A suitable Serum Protein Eletrophoresis protocol is outlined in Jenkins M. A., 1999 (Serum Protein Electrophoresis. In: Palfrey S. M. (eds) Clinical Applications of Capillary Electrophoresis. Methods in Molecular Medicine vol 27. Humana Press), incorporated herein by reference.

In a preferable embodiment, the serum is whole serum (e.g. whole animal serum). For example, the serum is preferably distinct from a fraction (e.g. an isolated fraction) obtainable from serum. An example of such fraction is Fraction V, also known as Bovine Serum Albumin (BSA).

In one embodiment, the charcoal-free solid agar medium comprises albumin (e.g. isolated albumin, such as Fraction V) at a concentration of less than 2% (w/v); preferably less than 1.5% (w/v), 1% (w/v), 0.5% (w/v), 0.4% (w/v), 0.3% (w/v), 0.2% (w/v), or 0.1% (w/v).

In one embodiment, the charcoal-free solid agar medium comprises albumin (e.g. isolated albumin, such as Fraction V) at a concentration of less than 20% (w/v); preferably less than 15% (w/v), 10% (w/v), 5% (w/v), 4% (w/v), 3% (w/v), 2% (w/v), 1% (w/v), 0.5% (w/v) or 0.2% (w/v).

The skilled person understands the term "agar medium". For example, the term "agar medium" may mean a solidified agar substance, typically comprising further agents for supporting the growth of a bacterium. The charcoal-free solid agar medium may be referred to as an "agar-based" medium.

The term agar embraces agarose. Agarose is one of the two principal components of agar, and may be purified from agar by removing the other principal component of agar, agaropectin.

The skilled person understands that an agar medium having an agar base is referred to as a solid culture medium. Therefore the charcoal-free solid agar medium of the present invention is referred to as a "solid" agar medium. The term "solid" may mean, for example, a gelled medium.

Therefore, the term "solid" means, for example, a culture medium having the consistency of an agar-based culture medium.

Preferably, the charcoal-free solid agar medium has an agar base, the agar base comprising the remaining components (e.g. serum) of the medium. For example, the remaining components may be admixed with an agar solution in a non-solid phase to provide an admixture, with said admixture subsequently being solidified into a solid phase (e.g. the agar base).

Without wishing to be bound by theory it is believed that serum components can be used to (e.g. selectively) absorb agents which are toxic to *Legionella* such as agar-derived toxins, thus preventing said toxins from suppressing *Legionella* growth. Thus, for example, the serum acts as a detoxifier in a charcoal-free solid agar medium of the invention. Therefore serum can be used as a substitute for charcoal (such as activated charcoal), which is highly surprising given that charcoal and serum differ substantially in structure and (traditional) function. However, unlike charcoal, serum does not (e.g. substantially) absorb antibiotics, such that antibiotics in the medium remain available to contact and interact with bacteria grown on the medium. Furthermore, the impact of serum on the colour of the medium is negligible, and far less pronounced than that of charcoal. A medium comprising charcoal has a deep, dark black colour making the identification of bacterial growth thereon difficult. At preferable concentrations of serum in the present invention, the effect on the colour of the media is negligible, such that the medium if substantially transparent.

A further key advantage of providing serum in a charcoal-free solid agar medium is that it provides a complex mixture of nutrients allowing for the growth of *Legionella*. This is supported by the observation that a solid medium consisting essentially of an agar base, serum and a nitrogen source (e.g. yeast extract) could support growth of *Legionella* (for example, certain components required for growth on BCYE, such as alpha-ketoglutarate, were not essential to support growth)—see Example 1. This is surprising, as it is was unexpected that the serum would provide nutrients for supporting the growth of *Legionella*.

Further key advantages of serum include low cost, and wide accessibility.

Without wishing to be bound by theory, the inventors believe the difficulties in identifying suitable component parts for a solid culture media has been due to the observation that *Legionella* growth is suppressed in the presence of many alkaline earth metal-containing salts and alkali metal-containing salt (e.g. NaCl), which are often found in prior art culture media, This susceptibility of *Legionella* to such alkaline earth metal-containing salts and alkali metal-containing salts was hitherto unknown, having been observed and demonstrated by the present inventors for the first time. The suppression effect of such alkaline earth metal-containing salts and alkali metal-containing salts is outlined in more detail below (e.g. in Example 8).

Thus, the ability to utilise serum (a previously unknown component part of solid agar media for *Legionella*) is all the more surprising in light of this observation. Another reason that it would not be expected that serum would be suitable for use in a *Legionella* medium is that serum comprises antibodies, which a skilled person may expect to inhibit *Legionalla*.

Advantageously, the inventors have found that a medium of the present invention supports growth of *Legionella* at similar levels to that of standard BCYE agar medium.

In one embodiment, wherein, following contact of the charcoal free solid agar medium with one or more *L. pneumophila* strain selected from NCTC 11233 and NCTC 11406, the charcoal-free solid agar supports the formation of a greater bacterial load compared with a control solid agar medium, wherein the control solid agar medium is charcoal-free and serum-free;

wherein the formation of a bacterial load is measured by an assay comprising:

i. contacting one or more *L. pneumophila* strain selected from NCTC 11233 and NCTC 11406 with:
   A. the charcoal-free solid agar medium to provide a test sample; and
   B. the control solid agar medium to provide a control sample;
ii. incubating the test sample and the control sample at 37° C. for 3, 4 or 5 days (preferably 5 days);
iii. comparing the bacterial load on the test sample subsequent to incubation with the bacterial load on the control sample subsequent to incubation; and
iv. confirming the charcoal-free solid agar medium supports the formation of a greater bacterial load compared with the control solid agar medium when the bacterial load on the test sample is higher compared to the bacterial load on the control sample.

NCTC 11233 (e.g. NCTC accession number: 11233) and NCTC 11406 (e.g. NCTC accession number: 11406) are strains of *L. pneumophila* obtainable from the National Collection of Type Cultures (NCTC) of Public Health England.

Thus, another aspect of the invention provides a charcoal-free solid agar medium for culturing *Legionella*, comprising:

a) serum, wherein the serum is present at a concentration of 1%-35% (v/v);

b) a nitrogen source; and c) an iron source;

wherein, following contact of the charcoal-free solid agar medium with one or more *L. pneumophila* strain selected from NCTC 11233 and NCTC 11406, the charcoal-free solid agar supports the formation of a greater bacterial load compared with a control solid agar medium, wherein the control solid agar medium is charcoal-free and serum-free;

wherein the formation of a bacterial load is measured by an assay comprising:

i. contacting one or more *L. pneumophila* strain selected from NCTC 11233 and NCTC 11406 with:

A. the charcoal-free solid agar medium to provide a test sample; and

B. the control solid agar medium to provide a control sample;

ii. incubating the test sample and the control sample at 37° C. for 3, 4, or 5 days (preferably 5 days);

iii. comparing the bacterial load on the test sample subsequent to incubation with the bacterial load on the control sample subsequent to incubation; and iv. confirming the charcoal-free solid agar medium supports the formation of a greater bacterial load compared with the control solid agar medium when the bacterial load on the test sample is higher compared to the bacterial load on the control sample.

The control solid agar culture medium may comprise:

a) agar at a concentration of 1-2% (w/v);

b) proteose peptone at a concentration of 1-2% (w/v);

c) albumin (preferably bovine serum albumin) at a concentration of 2-4% (w/v), or 15-25% (w/v);

d) yeast extract at a concentration of 0.05-0.2% (w/v);

e) ACES buffer at a concentration of 0.5-2% (w/v);

f) ferric pyrophosphate at a concentration of 0.01-0.05% (w/v); and g) alpha-ketogluarate at a concentration of 0.05-0.2% (w/v).

In one embodiment, the control medium may be LTM medium, as described in Armon and Payment, Journal of Microbiological Methods 11 (1990), pages 65-71 (incorporated herein by reference).

In one embodiment, an azithromycin antibiotic has a $MIC^{50}$ of 0.02-0.04 μg/ml against a *Legionella pneumophila* bacterium cultured on a charcoal-free solid agar medium, wherein said $MIC^{50}$ is measured by an assay comprising:

a) contacting a culture of *Legionella pneumophila* with a first sample of the charcoal-free solid agar medium, wherein the first sample comprises an azithromycin antibiotic at a concentration of 0.02-0.04 μg/ml;

b) contacting the culture of *Legionella pneumophila* with a second sample of the charcoal-free solid agar medium, wherein the second sample does not comprise an azithromycin antibiotic;

c) incubating the first sample and the second sample at 37° C. for 5 days; and d) confirming that the azithromycin antibiotic has a $MIC^{50}$ of 0.02-0.04 μg/ml against a *Legionella pneumophila* bacterium when the bacterial load on the first sample is at least 50% lower than the bacterial load on the second sample; preferably wherein the bacterial load on the first sample is 50% lower than the bacterial load on the second sample.

For convenience, said $MIC^{50}$ may be expressed as an average $MIC^{50}$ from a series of assays performed in an identical manner.

In one embodiment, a *Legionella pneumophila* bacterium cultured on said charcoal-free solid agar medium has increased susceptibility to an azithromycin antibiotic when compared with a *Legionella pneumophila* bacterium cultured under equivalent conditions on a control solid agar medium comprising Buffered Yeast Extract and water-lysed horse blood, wherein said control is serum-free.

In one embodiment, the charcoal-free solid agar culture medium has improved culturing activity for two or more *Legionella* strains when compared with a control solid agar culture media, wherein the control solid agar culture media is charcoal-free and serum-free; wherein the culturing activity is measured by an assay comprising:

a) contacting a culture of the *Legionella* with:

i. the charcoal-free solid agar culture medium to provide a test sample; and ii. the control solid agar culture medium to provide a control sample;

b) incubating the test sample and the control sample at 37° C. for 3 days;

c) comparing the bacterial load on the test sample subsequent to incubation with the bacterial load on the control sample subsequent to incubation; and d) identifying the charcoal-free solid agar culture medium as having improved culturing activity when the bacterial load on the test sample is higher compared to the bacterial load on the control sample.

In one embodiment, the charcoal-free solid agar culture medium is capable of supporting the growth of one or more *L. pneumophila* strain selected from NCTC 11233 and NCTC 11406 when incubated at 37° C. for 5 days.

In one embodiment, a *Legionella pneumophila* bacterium cultured on said solid microbiological culture medium has increased susceptibility to an azithromycin antibiotic when compared with a *Legionella pneumophila* bacterium cultured under equivalent conditions on a control solid microbiological culture medium comprising Buffered Yeast Extract and water-lysed horse blood, wherein said control is serum-free.

In one embodiment, the charcoal-free solid agar culture medium is effective for culturing at least 35 species of *Legionella*.

Preferably, the charcoal-free solid agar medium is substantially transparent (e.g. is transparent). Suitably, the charcoal-free solid agar medium retains the natural colour of the agar (i.e. agar absent any of the other constituent parts). A substantially transparent medium is ideally suited to monitoring growth by turbidometric means (e.g. using a standard laboratory spectrophotometer), including automated monitoring of growth by optical density change. Substantially transparent media are also suited to detection assays that involve a colour-change, such as biochemical assays for detecting a metabolic product of a *Legionella* bacterium.

Furthermore, the growth of bacterial colonies on a charcoal-free solid agar medium of the present invention is readily identifiable.

In one embodiment, a charcoal-free solid agar medium of the invention is colourless.

In one embodiment, a charcoal-free solid agar medium exhibits low background auto-fluorescence. Culture media having low fluorescence are particularly suited for use in fluorescence assays—for example, assays for detecting the presence of macromolecules, such as DNA, that have been secreted by the cultured bacteria into the medium.

The transparent and/or colourless nature of the present charcoal-free solid agar medium is achievable as the culture medium does not rely on the presence of charcoal (e.g. activated charcoal) or blood (e.g. whole blood, comprising red blood cells). Media which comprise activated charcoal have a deep, dark colour making the identification of bacterial growth difficult. Media which comprise blood (e.g. whole blood or lysed blood) tend to have a deep, dark red colour leading to with similar difficulties in identifying bacterial growth. In contrast, serum is substantially transparent.

Furthermore, the present inventors have surprisingly found that the present charcoal-free solid agar medium is suitable for use in methods for identifying *Legionella* antibiotics. Media comprising charcoal are known to lack suitability in such methods due to the absorptive effects of charcoal.

In one embodiment a charcoal-free solid agar medium of the present invention does not comprise blood. The term "blood" as used herein excludes reference to serum (e.g. isolated serum), for example, the serum being a fraction of blood, separated from the remaining components/fractions of blood. The term blood embraces difibrinated blood and lysed blood, such as water-lysed blood.

Preferably, serum used in a charcoal-free solid agar medium of the invention is free of (or substantially free of) white blood cells, red blood cells and/or fibrinogens. In a preferable embodiment, the term serum means a serum component of blood that has been previously separated from the remaining components of blood (e.g. plasma).

Furthermore, it is known that the effectiveness of antibiotics varies under different growth conditions. As the charcoal-free solid agar medium of the invention does not rely on the presence of complex constituents such as blood (e.g. whole blood), it is therefore possible to grow *Legionella* under more physiologically relevant growth conditions, thus allowing for identification of clinically useful antibiotics. Hence, the results of susceptibility testing with respect to antibiotics are more reliable when *Legionella* are grown on a charcoal-free solid agar medium of the invention.

An antibiotic may be incorporated into the charcoal-free solid agar medium to investigate the antibiotic's effect on the growth of *Legionella* spp. Said antibiotic may be incorporated into a culture medium of the present invention at a range of predetermined concentrations, in order to determine the minimum inhibitory concentration (MIC) (e.g. MIC50 and MIC90) and, with subculture (e.g. at 24 h or 48 hr), the minimum bactericidal concentration (MBC) of the antibiotic.

Preferably, said antibiotic is a candidate antibiotic to be screened for its suitability as a *Legionella* antibiotic.

Thus, the culturing means and methods described herein advantageously find utility in methods for screening for antibiotics which target *Legionella.*

In aspects and embodiment related to a screening method described herein, the candidate antibiotic may be present in the charcoal-free solid agar medium at a concentration of about 0.00001 mg/L to 10 mg/L, 0.0001 mg/L to 9 mg/L, 0.001 mg/L to 8 mg/L, 0.01 mg/L to 7 mg/L, 0.1 mg/L to 6 mg/L, 1 mg/L to 5 mg/L, or 2 mg/L to 4 mg/L. The candidate antibiotic may be present in the charcoal-free solid agar medium at a concentration of about 0.005 mg/L to 0.07 mg/L. The candidate antibiotic may be present in the charcoal-free solid agar medium at a concentration of about 0.004 mg/L to 0.04 mg/L. The candidate antibiotic may be present in the charcoal-free solid agar medium at a concentration of about 0.015 mg/L to 2 mg/L. The candidate antibiotic may be present in the charcoal-free solid agar medium at a concentration of about 0.03 mg/L to 1 mg/L. The candidate antibiotic may be present in the charcoal-free solid agar medium at a concentration of about 0.004 mg/L to 0.07 mg/L. The candidate antibiotic may be present in the charcoal-free solid agar medium at a concentration of about 0.0001 mg/L to 0.001 mg/L. The candidate antibiotic may be present in the charcoal-free solid agar medium at a concentration of about 0.1 mg/L to 2 mg/L.

Bacterial growth may be identified as a colony and/or streak of bacteria on the solid microbiological culture medium.

The use of solid medium (e.g. agar medium) for growing *Legionella* when screening antibiotics has been impeded (e.g. prevented) by the fact that agar-medium has traditionally required the presence of charcoal (e.g. activated charcoal) to allow growth on agar. Charcoal absorbs antibiotics, thus preventing a faithful investigation of their effect on the growth of *Legionella* on media which comprise charcoal.

However, the use of solid medium (e.g. agar medium) for growing bacteria is highly advantageous for screening antibiotics. For example, solid medium allows the use of an automated multipin inoculator to examine multiple (e.g. 80) species/strains at a time for a range of antibiotic concentrations without requirement to sterilise the inoculator in between inoculation to differing culture media with differing antibiotic concentrations. This allows significant scale-up and automation to be utilised. This demonstrates a yet further advantage of the charcoal-free solid agar medium of the invention.

The *Legionella* may be inoculated on a charcoal-free solid agar medium lacking a candidate antibiotic, with said candidate antibiotic being subsequently applied to the inoculum.

In one aspect there is provided a screening method for identifying a *Legionella* antibiotic, comprising:

a) contacting said *Legionella* with a charcoal-free solid agar medium that comprises:
    i. serum, wherein the serum is present at a concentration of 1%-35% (v/v; and
    ii. a nitrogen source; and
    iii. an iron source;
b) contacting the *Legionella* present on the charcoal-free solid agar medium with a candidate antibiotic;
c) incubating the *Legionella* in the presence of said candidate antibiotic; and
d) identifying the presence or absence of suppressed bacterial growth;

wherein the presence of suppressed bacterial growth indicates said candidate antibiotic is a *Legionella* antibiotic, and wherein the absence of suppressed bacterial growth indicates said candidate antibiotic is not a *Legionella* antibiotic.

In one embodiment, said screening method further comprises comparing bacterial growth in the presence of said candidate antibiotic with bacterial growth in a control sample incubated in the absence of said candidate antibiotic. Preferably, suppressed bacterial growth means that bacterial growth in the presence of said candidate antibiotic is reduced when compared with bacterial growth in the control sample.

Said incubation may be for between 1-7 days, 2-6 days of 3-5 days. Preferably, said incubation may be for between 3-5 days. A suitable incubation time is 5 days. Said incubation is suitably performed at a temperature of between about 30° C.-40° C., preferably about 37° C.

The skilled person understands that where the methods of the invention comprise a comparison step between two samples (e.g. between a "test sample" and a "control sample") that conditions (e.g. assay conditions during the method) should be kept consistent. For example, the bacterial load (e.g. starting bacterial load) of *Legionella* provided in the contacting step (contacting *Legionella* with a solid microbiological culture medium) in both the test sample and control sample should be substantially the same, as should incubation times and temperature, etc.

The bacterial load of a *Legionella* in a control sample may be determined either within (i.e. constituting a step of) or externally to screening methods of the invention. In one embodiment, the screening methods of the invention comprise a step of incubating a control sample in the absence of an antibiotic. In one embodiment, the bacterial load in a control sample is obtained externally to a method of the invention and accessed during the comparison step of the present invention.

In one embodiment, a screening method of the invention further comprises the step of recording the data obtained in said method on a suitable data carrier.

In one embodiment, the nitrogen source is one or more selected from yeast extract, beef extract, liver extract, casein hydrolysate, plant cell extract, soy bean extract, or any combination thereof. Such nitrogen source(s) may further provide a carbon source, such that a charcoal-free solid agar medium described herein may further comprise a carbon source.

The term "nitrogen source" may be used synonymously with the term "amino acid source" herein. For example, the nitrogen source may comprise nitrogen for synthesising amino acids (and optionally lack an amino acid), the amino acids being synthesised by the *Legionella* bacterium.

A nitrogen source is preferably a solid (e.g. fixed) nitrogen in an organic or inorganic form. The nitrogen source may comprise nitrate or nitrite salts, and more preferably comprises amino acids, peptides, peptones, and/or proteins.

In a preferable embodiment, the nitrogen source is a yeast extract.

The skilled person understands that a "yeast extract" is typically obtained by centrifuging a culture of lysed and/or degraded yeast cells, with the resulting supernatant comprising (or consisting of) the yeast extract.

Any serum suitable for use in a charcoal-free solid agar medium may be comprised within a culture medium according to the present invention.

In one embodiment, a serum is a synthetic serum. A synthetic serum is typically a serum which has been manufactured using component parts present in serum (electrolytes, antibodies, antigens and hormones).

In a preferable embodiment, the serum is an animal serum.

In one embodiment, a serum is one or more selected from horse serum, sheep serum, goat serum, bovine serum, fetal bovine serum, calf serum, mouse serum, rat serum, pig serum, guinea pig serum, porcine serum and rabbit serum. In one embodiment, a serum is one or more selected from horse serum, bovine serum, and fetal bovine serum.

In a preferable embodiment, a serum is horse serum.

In one embodiment, the charcoal-free solid agar medium comprises a serum at a concentration of 1%-35% (v/v). For example, the serum may be at a concentration of 5%-35% (v/v), 10%-30% (v/v), or 15%-25% (v/v). In one embodiment, the serum is present at a concentration of 8%-12% (v/v). In a preferable embodiment, a serum is present at a concentration of about 10% (v/v). Said % values refer to the % of the final volume of the charcoal-free solid agar medium.

In one embodiment, a nitrogen source is present in the charcoal-free solid agar medium at a concentration of 0.2%-10% (w/v). For example, the nitrogen source may be present at a concentration of 0.5%-8% (w/v), 0.8%-6% (w/v), 1%-4% (w/v), or 2%-3% (w/v). In one embodiment, a nitrogen source is present at a concentration of 0.8%-1.2% (w/v). In a preferable embodiment, a nitrogen source is present at a concentration of about 1% (w/v). Said percentage values refer to the % of the final volume of the charcoal-free solid agar medium.

In one embodiment, said charcoal-free solid agar medium further comprises a buffer. Preferably, said buffer is selected from N-(2-Acetamido)-2-aminoethanesulfonic acid (ACES) buffer, potassium hydroxide, or a combination thereof.

In one embodiment, a buffer is present in a charcoal-free solid agar medium at a concentration of about 1 mM to about 500 mM. For example, a buffer may be present at a concentration of 10 mM-350 mM, 20 mM-200 mM, 30 mM-100 mM, or 40 mM-100 mM. In one embodiment, a buffer is present in a charcoal-free solid agar medium at a concentration of 45 mM-55 mM. In one embodiment, a buffer is present in a charcoal-free solid agar medium at a concentration of 15 mM-25 mM. In a preferable embodiment, a buffer is present in a charcoal-free solid agar medium at a concentration of about 20 mM.

In one embodiment, an iron source is present in a charcoal-free solid agar medium at a concentration of 0.001%-1% (w/v). For example, the iron source may be present at a concentration of 0.002%-0.8% (w/v), 0.003%-0.6% (w/v), 0.004%-0.4% (w/v), or 0.005%-0.2% (w/v). In one embodiment, and iron source is present at a concentration of 0.01%-0.1% (w/v). In one embodiment, an iron source is present at a concentration of 0.002%-0.003% (w/v). In one embodiment, an iron source is present in a culture medium at a concentration of 0.015%-0.04% (w/v). In a preferable embodiment, an iron source is present at a concentration of about 0.025% (w/v). Said percentage values refer to the % of the final volume of the charcoal-free solid agar medium.

In one embodiment, an iron source is present at a concentration of about 0.05 g/L to 2 g/L, about 0.1 g/L to about 1.8 g/L, about 0.15 g/L to about 1.6 g/L, about 0.2 g/L to about 1.4 g/L, about 0.25 g/L to about 1.2 g/L, about 0.3 g/L to about 1 g/L, about 0.35 g/L to about 0.8 g/L, or about 0.4 g/L to about 0.6 g/L. In one embodiment, an iron source is present at a concentration of about 0.15 g/L to about 0.35 g/L. In a preferable embodiment, an iron source is present in a culture medium at a concentration of about 0.25 g/L.

In one embodiment, said iron source is one or more selected from an iron chelate and ferric pyrophosphate. Preferably, the iron source may be ferric pyrophosphate.

In one embodiment, said culture medium further comprises alpha-ketoglutarate.

In one embodiment, an alpha-ketoglutarate is present in a charcoal-free solid agar medium at a concentration of 0.001%-1% (w/v). For example, the alpha-ketoglutarate may be present at a concentration of 0.002%-0.8% (w/v), 0.003%-0.6% (w/v), 0.004%-0.4% (w/v), 0.005%-0.2% (w/v), or 0.006%-0.18% (w/v). In one embodiment, an alpha-ketoglutarate is present at a concentration of 0.005%-0.02% (w/v). In a preferable embodiment, an alpha-ketoglutarate is present at a concentration of about 0.01% (w/v). Said percentage values refer to the % of the final volume of the charcoal-free solid agar medium.

In one embodiment, an alpha-ketoglutarate is present at a concentration of about 0.05 g/L to about 3 g/L, about 0.1 g/L to about 2.5 g/L, about 0.15 g/L to about 2 g/L, about 0.2 g/L to about 1.5 g/L, about 0.25 g/L to about 1 g/L, or about 0.3 g/L to about 0.5 g/L. In one embodiment, an alpha-ketoglutarate is present at a concentration of about 0.5 g/L to about 1.5 g/L. In a preferable embodiment, an alpha-ketoglutarate is present at a concentration of about 1 g/L.

In one embodiment, said culture medium further comprises cysteine. Preferably, said cysteine is L-Cysteine.

In one embodiment, a cysteine (e.g. L-Cysteine) is present in a charcoal-free solid agar medium at a concentration of 1%-10% (w/v). For example, the cysteine may be present at a concentration of 2%-9% (w/v), 3%-8% (w/v), or 4%-7% (w/v). In one embodiment, a cysteine is present at a concentration of 3%-5% (w/v). In a preferable embodiment, a cysteine is present at a concentration of about 4% (w/v). Said percentage values refer to the % of the final volume of the charcoal-free solid agar medium.

In one embodiment, a cysteine (e.g. L-Cysteine) is present in a charcoal-free solid agar medium at a concentration of 0.001%-2% (w/v). For example, the cysteine may be present at a concentration of about 0.002%-1.8% (w/v), 0.003%-1.6% (w/v), 0.004%-1.4% (w/v), 0.005%-1.2% (w/v), 0.006%-1% (w/v), 0.008%-0.8% (w/v), 0.01%-0.6% (w/v), 0.02%-0.6% (w/v), or 0.04%-0.4% (w/v). In one embodiment, a cysteine is present at a concentration of 0.03%-0.05% (w/v). In a preferable embodiment, a cysteine is present in at a concentration of about 0.04% (w/v). Said percentage values refer to the % of the final volume of the charcoal-free solid agar medium.

In one embodiment, a cysteine (e.g. L-Cysteine) is present in a culture medium at a concentration of about 1 g/L to about 100 g/L, about 5 g/L to about 90 g/L, about 15 g/L to about 80 g/L, about 20 g/L to about 70 g/L, about 25 g/L to about 60 g/L, about 30 g/L to about 50 g/L, or about 35 g/L to about 40 g/L. In one embodiment, an cysteine is present in a culture medium at a concentration of about 30 g/L to about 50 g/L. In a preferable embodiment, a cysteine is present in a culture medium at a concentration of about 40 g/L.

In one embodiment, agar is present in a charcoal-free solid agar medium at a concentration of 0.2%-10% (w/v). In one embodiment, agar is present in a charcoal-free solid agar medium at a concentration of 0.2%-5% (w/v). For example, the agar may be present at a concentration of 0.5%-8% (w/v), 0.8%-6% (w/v), 1%-4% (w/v), or 2%-3% (w/v). In one embodiment, agar is present at a concentration of about 0.8%-1.2% (w/v). In a preferable embodiment, agar is present in a culture medium at a concentration of about 1% (w/v). Said percentage values refer to the % of the final volume of the charcoal-free solid agar medium.

Said agar is suitably utilised to provide a solid culture medium.

Preferably, the agar of the present medium has not been pre-washed (e.g. with water) for example subsequent to autoclaving of the agar.

In one embodiment, said agar is one or more selected from select agar and differential agar. In a preferable embodiment, said agar is select agar.

The agar has preferably been sterilized e.g. by autoclaving. Thus, in a preferable embodiment said agar is autoclaved agar.

The agar may be (e.g. may have been) autoclaved at a temperature in the range of 80° C.-150° C., 90° C.-140° C., 100° C.-130° C. The agar may be (e.g. may have been) autoclaved at a temperature in the range of 115° C.-125° C., preferably at 121° C. The agar may be (e.g. may have been) autoclaved for 5, 10, 15, 20, 25, 35, 50, 75 or 100 minutes, preferably for 15 minutes.

All other components of the culture medium are preferably sterilised e.g. by passage through a filter. For example, a serum may be serum which has been subjected to filtration, preferably prior to incorporation into the charcoal-free solid agar medium (e.g. into the agar base of the culture medium).

Suitably, said filter is a micron (μm) filter and may have a pore size of about 1 μm, 0.8 μm, 0.6 μm, 0.4 μm or 0.2 μm. In a preferable embodiment, said filter (e.g. micron filter) has a pore size of about 0.22 μm.

A suitable filter steriliser may be the Corning® 500 mL vacuum filter/storage bottle system with a 0.22 μM pore.

Suitably, all components of a culture medium of the present are mixed with water (e.g. double distilled water) at an appropriate volume.

A preferable culture medium of the invention is outlined in the table below (see Table 1). Thus, a charcoal-free solid agar medium of the invention may comprise or consist of:

TABLE 1

| Component | Concentration | g/L |
|---|---|---|
| Horse serum | 10% | 100 g/L |
| Yeast extract | 1% | 10 g/L |
| N-(2-Acetamido)-2-aminoethanesulfonic acid (ACES) buffer | 20 mM | ~3.6 g/L |
| Ferric pyrophosphate | 0.025% | 0.25 g/L |
| alpha-ketoglutarate | 0.01% | 1 g/L |
| L-Cysteine | 4% | 40 g/L |
| Select Agar | 1% | 10 g/L |

Said ingredients are suitably admixed in distilled water ($dH_2O$) or double distilled water ($ddH_2O$) to bring the medium to its final volume for preparation. For example, a medium comprising 1% yeast extract comprises about 10 g or yeast extract per liter of $dH_2O$ or $ddH_2O$.

The pH of the culture medium may be adjusted (e.g. with a pH adjusting agent) to between 5.5 to 8, or 6.5 to 7.5. For example, the pH of the culture medium may be adjusted to about 6.0. In embodiments where the pH is adjusted, the value (concentration and/or g/1) referred in Table 1 (or elsewhere in the present description) are the values present prior to addition of (e.g. dilution with) the pH adjusting agent. Preferably, the pH adjusting agent is potassium hydroxide (KOH).

In one embodiment, a charcoal-free solid agar medium comprises a pH of between 5.5 to 8. In one embodiment, a charcoal-free solid agar medium comprises a pH of between 6.5 to 7.5.

A preferable charcoal-free solid agar medium may comprise or consist of the components present in Table 1, admixed in $ddH_2O$ for preparation. Preferably, the pH of the culture medium is between 6.5 to 7.5, more preferably about pH 6.9.

Thus, in one embodiment the charcoal-free agar medium (e.g. of any method of the present invention) comprises or consists of horse serum at a concentration of about 10% (v/v), yeast extract at a concentration of about 1% (w/v), ACES buffer at a concentration of about 20 mM, ferric pyrophosphate at a concentration of about 0.025% (w/v), alpha-ketoglutarate at a concentration of about 0.01% (w/v), L-cysteine at a concentration of about 4% (w/v), and $ddH_2O$ to bring the volume of the medium to 100% (v/v). Suitably, the pH of the culture medium is pH 6.9.

Reference to the pH of the culture medium means the pH of the medium prior to inoculation of bacteria.

In one aspect, there is provided a charcoal-free solid agar medium for culturing *Legionella*, comprising or consisting of:

a) agar at a concentration of 0.5%-2% (w/v);
b) serum at a concentration of 5%-15% (v/v);
c) yeast extract at a concentration of 0.5%-2% (w/v);
d) ACES buffer at a concentration of 15 mM-25 mM;
e) ferric pyrophosphate at a concentration of 0.015%-0.035% (w/v);
f) alpha-ketoglutarate at a concentration of 0.005%-0.05% (w/v); and
g) L-cysteine at a concentration of 2%-6% (w/v).

A suitable select agar may be select agar available from Sigma Aldrich—Cat. No. A5054. A suitable yeast extract may be yeast extract available from Sigma Aldrich—Cat. No. 07533. A suitable L-cysteine is L-cysteine available from Sigma Aldrich—Cat. No. W326305. A suitable ACES buffer may be ACES buffer available from Sigma Aldrich—Cat. No. A9758. A suitable ferric pyrophosphate may be ferric pyrophosphate available from Sigma Aldrich—Cat. No. P6526. A suitable alpha-ketoglutarate may be alpha-ketoglutarate available from Sigma Aldrich—Cat. No. 75890.

In one embodiment, the charcoal-free solid agar medium may comprise and indicator, reagent and/or substrate to demonstrate enzyme activity, useful for identifying bacteria culture therein. Thus, in one embodiment the present charcoal-free solid agar medium may be used for biochemical identification of a bacterium, wherein the charcoal-free solid agar medium comprises an indicator to confirm the presence of said bacterium. Preferably, the charcoal-free solid agar medium is substantially transparent, and thus ideally suited to demonstrating the colour changes typically used in clinical laboratories as end-points for such tests.

Suitably, said indicator is a dye. Preferable dyes include bromcresol purple and bromthymol blue.

Suitably, a charcoal-free solid agar medium of the present invention may be present within a kit adapted for culturing *Legionella*. Thus, one aspect of the inventions provides a kit comprising a culture-medium of the present invention for culturing *Legionella*, wherein said culture medium provides a means for culturing *Legionella* in the presence of agar-derived toxins; and wherein said kit comprises instructions to use said culture medium to culture a *Legionella* bacterium.

For example, one aspect of the invention provides a kit comprising a charcoal-free solid agar medium for culturing *Legionella*, wherein said charcoal-free solid agar medium comprises:

a) serum, wherein the serum is present at a concentration of 1%-35%;
b) a nitrogen source; and
c) an iron source;

preferably wherein said kit further comprises instructions for culturing a *Legionella* bacterium on said charcoal-free solid agar medium.

Another aspect provides a kit comprising reagents for preparing a charcoal-free solid agar medium for culturing *Legionella*, wherein said reagents comprise:

a) agar;
b) serum;
c) a nitrogen source; and
d) an iron source; and preferably wherein said kit further comprises instructions for culturing a *Legionella* bacterium on said charcoal-free solid agar medium.

Any culture medium described herein may be comprised within said kit.

Said kit may further comprise a housing for containing the culture medium or one or more of the component parts thereof.

Said kit may suitably be used for culturing *Legionella*. Thus, the invention embraces use of a kit described herein for culturing *Legionella*.

The culturing means and methods provided by the present invention can be employed for isolating a *Legionella* from a sample for detecting for contamination with *Legionella*, or for diagnosing an infection with *Legionella* in a subject.

Thus, in one aspect there is provided a method for detecting the presence or absence of a *Legionella* in a sample, comprising:

a. contacting said sample with a charcoal-free solid agar medium that comprises:
   i. a serum;
   ii. an amino acid source; and
   iii. agar;
b. incubating said charcoal-free solid agar medium; and
c. identifying the presence or absence of bacterial growth on said charcoal-free solid agar medium;
   wherein the presence of bacterial growth is indicative of the presence of *Legionella* in said sample, and the absence of bacterial growth is indicative of the absence of *Legionella* in said sample.

Bacterial growth may suitably be identified as a streak and/or colony of bacteria growing on a surface of the culture medium.

In one aspect there is provided a method for diagnosing a *Legionella* infection in a subject, said method comprising:

a. obtaining an isolated sample from said subject;
b. contacting said sample with a charcoal-free solid agar medium that comprises:
   i. serum, wherein the serum is present at a concentration of 1%-35% (v/v);
   ii. a nitrogen source; and
   iii. an iron source;
c. incubating the charcoal-free solid agar medium; and
d. identifying the presence or absence of bacterial growth on said charcoal-free solid agar medium;
   wherein the presence of bacterial growth is indicative of the presence of a *Legionella* infection in the subject, and the absence of bacterial growth is indicative of the absence of a *Legionella* infection in the subject.

The term "diagnosis" as used herein encompasses identification, confirmation and/or characterisation of *Legionella* infection. Methods of diagnosis according to the invention are useful to confirm the existence of an infection. Methods of diagnosis are also useful in methods for assessment of clinical screening, prognosis, choice of therapy, evaluation of therapeutic benefit, i.e. for drug screening and drug development. Efficient diagnosis allows rapid identification of the most appropriate treatment (thus lessening unnecessary exposure to harmful drug side effects), and reducing relapse rates.

The terms "subject", "individual" and "patient" are used interchangeably herein to refer to a mammalian subject. In one embodiment the "subject" is a human, a companion animal (e.g. a pet such as dogs, cats, and rabbits), livestock (e.g. pigs, sheep, cattle, and goats), and horses. In a preferable embodiment, the subject is a human. In methods of the invention, the subject may not have been previously diagnosed as having *Legionella* infection. Alternatively, the subject may have been previously diagnosed as having a *Legionella* infection. The subject may also be one who exhibits disease risk factors, or one who is asymptomatic for *Legionella* infection. The subject may also be one who is suffering from or is at risk of developing *Legionella* infection. In one embodiment, the subject has been previously administered a *Legionella* therapy.

A "sample" for use in the present invention may be any sample that comprises or is suspected of comprising a *Legionella* bacterium or fragment thereof. Suitably, said sample may be isolated from a subject suspected of having an infection with *Legionella*. In some embodiments, the sample is isolated from a subject diagnosed as having a *Legionella* infection. Suitably, a sample may be selected from blood, urine, eye fluid, lymphatic fluid, saliva, synovial fluid, seminal fluid, cerebrospinal fluid, sebaceous secretions, and/or sputum.

In one embodiment, the sample is obtained from surgical or other medical equipment. In one embodiment, the sample is an environmental sample (e.g. water, soil and/or sediment). In a preferable embodiment, the sample is a water sample.

In one embodiment, a sample may be processed to isolate a *Legionella* bacterium from a sample prior to detecting the presence or absence of a *Legionella* bacterium.

In one aspect, the present charcoal-free solid agar medium may be used as a clinical enrichment medium for recovering *Legionella* bacteria. For example, the bacteria may be recovered in low numbers from bodily fluids such as saliva. By way of example, the culture medium may be inoculated (preferably using ascetic technique) with an aliquot of an appropriate clinical sample in order to identify the presence of *Legionella* in that sample.

Optionally, the charcoal-free solid agar medium may be used to produce a selective medium. A selective medium comprises one or more "selection agents", which are components which prevent that suppress (e.g. inhibit or prevent) the growth of a certain genus/species of bacteria and/or promote the growth of a desired genus/species, thereby allowing the growth of a bacterium from one genus/species from a mixed inoculum.

Thus, in one embodiment a charcoal-free solid agar medium of the present invention further comprises an antibiotic, preferably an antibiotic which does not inhibit the growth of a *Legionella* bacterium. By way of example, antibiotics such as vancomycin, amphotericin B, nystatin or trimethoprim may be added to the solid microbiological culture medium. In this regard, antibiotics such as vancomycin inhibit Gram-positive bacteria, antibiotics such as amphotericin B and nystatin inhibit fungi, and antibiotics such as trimethoprim prevent the swarming of *Proteus* spp. These antibiotics may be useful for inhibiting bacteria from sites that have normal flora present, that could compete with and potentially overgrow *Legionella* bacteria.

Said antibiotic may be one or more selected from cephalothin, colistin, vancomycin and cycloheximide. Suitably, the antibiotic is one or more selected from polymyxin B, cefamandole and anisomycin.

Species of *Legionella* show good growth on the present medium. In one embodiment, the growth of a *Legionella* bacterium on said charcoal-free solid agar medium is at least 80% (e.g. at least 85%, 90% or 95%) equivalent to the growth of a *Legionella* bacterium on a BCYE agar medium. The skilled person understands that "BCYE medium" is a traditional solid medium for culturing *Legionella*. BCYE typically comprises or consists of activated charcoal (2 g/L), yeast extract (1%), ACES buffer (50 mM), ferric pyrophosphate (0.25 g/L), alpha-ketoglutarate (1 g/L), L-cysteine (40 g/L), agar (e.g. select agar) (1%), and $ddH_2O$ (the remaining %, bring the total to 100%). A BCYE agar is described in Feeley et. al., 1979 (J. Clin. Microbiol. 10, 437-441) and Pasculle et. al., 1980 (J. Infect. Dis. 141, 727-732), both of which are incorporated herein by reference.

In one embodiment, said charcoal-free solid agar medium is effective for culturing at least 35 (e.g. at least 40, 50, 55, 60, or 65) species of *Legionella.*

The present medium is particularly suitable for testing the susceptibility of *Legionella* to antibiotics. In one embodiment, a *Legionella pneumophila* bacterium cultured on said charcoal-free solid agar medium has increased susceptibility to an azithromycin antibiotic when compared with a *Legionella pneumophila* bacterium cultured under equivalent conditions on a control medium comprising Buffered Yeast Extract and water-lysed horse blood, preferably wherein said control medium is serum free (e.g. lacks serum). Said "Buffered Yeast Extract and water-lysed horse blood" may comprise or consist of yeast extract (1% w/v), ACES buffer (50 mM), ferric pyrophosphate (0.25 g/L), alpha-ketoglutarate (1 g/L), L-cysteine (40 g/L), agar (e.g. select agar) (1% w/v), water-lysed horse blood (10% v/v) and $ddH_2O$ (the remaining %, bring the total to 100%).

In one embodiment, a $MIC^{50}$ for an azithromycin antibiotic for a *Legionella pneumophila* bacterium cultured on said charcoal-free solid agar medium is <0.06 mg/mi. The $MIC^{50}$ is the lowest concentration of antibiotic (e.g. azithromycin) which reduces growth of a bacterium by 50% compared to a growth on a control cultured in the absence of said antibiotic, but under otherwise equivalent conditions. This is suitably tested with an 'azithromycin screen' comprising (a) contacting a *Legionella pneumophila* with a charcoal-free solid agar medium of the present invention, said charcoal-free solid agar medium comprising an azithromycin antibiotic at a concentration of at least 0.005 mg/L; (b) incubating said medium; and (c) repeating steps (a)-(b) iteratively, wherein the medium in each iterative step comprises an increased concentration of said azithromycin antibiotic (e.g. 0.01 mg/ml, 0.03 mg/L, 0.08 mg/L, 0.1 mg/L, or 0.25 mg/L) until the concentration of said azithromycin antibiotic which reduces growth of a bacterium by 50% compared to growth on a control incubated in the absence of said antibiotic is determined. Said *Legionella pneumophila* may be of serogroup 1.

In one embodiment, a charcoal-free solid agar medium of the invention comprises a red blood cell content of less than 4.5% (v/v) (e.g. less than 4%, 3%, 2% or 1% (v/v)).

A *Legionella* bacterium may be any species of the genus *Legionella*. In one embodiment, a *Legionella* is one or more selected from the following species: *Legionella adelaidensis, L. anisa, L. beliardensis, L. birminghamensis, L. bozemanae, L. brunensis, L. busanensis, L. cardiac, L. cherrii, L. cincinnatiensis, L. clemsonensis, L. donaldsonii, L. drancourtii, L. dresdenensis, L. drozanskii, L. dumoffii, L. erythra, L. fairfieldensis, L. fallonii, L. feeleii, L. geestiana, L. genomospecies, L. gormanii, L. gratiana, L. gresilensis, L. hackeliae, L. impletisoli, L. israelensis, L. jamestowniensis, Candidatus L. jeonii, L. jordanis, L. lansingensis, L. londiniensis, L. longbeachae, L. lytica, L. maceachemii, L. massiliensis, L. micdadei, L. monrovica, L. moravica, L. nagasakiensis, L. nautarum, L. norrlandica, L. oakridgensis, L. parisiensis, L. pittsburghensis, L. pneumophila, L. quateirensis, L. quinlivanii, L. rowbothamii, L. rubrilucens,*

*L. sainthelensi, L. santicrucis, L. shakespearei, L. spiritensis, L. steelei, L. steigerwaltii, L. saoudiensis, L. taurinensis, L. thermalis, L. tucsonensis, L. tunisiensis, L. wadsworthii, L. waltersii, L. worsleiensis, L. yabuuchiae.*

In one embodiment, a *Legionella* is one or more selected from the following species: *L. adelaidensis, L. anisa, L. beliardensis, L. birminghamensis, L. bozemanae, L. brunensis, L. busanensis, L. cherrii, L. cincinnatiensis, L. donaldonsii, L. dresdeniensis, L. dumoffii, L. erythra, L. fairfieldensis, L. feeleii, L. geestiana, L. gormanii, L. gratiana, L. gresilensis, L. hackeliae* sg1, *L. impletisoli, L. israelensis, L. jamestowniensis, L. jordanis, L. lansingensis, L. londiniensis, L. longbeachae, L. maceachemii, L. micdadei, L. micdadei, L. moravica, L. pneumophila, L. nagasakiensis, L. taurinensis, L. wadsworthii, L. yabuuchiae, L. geestiana, L. wadsworthii, L. gormanii, L. yabuuchiae, L. gratiana, L. nautarum, L. oakridgensis, L. parisiensis, L. quateirensis, L. quinlivanii* sg1, *L. quinlivanii* sg2, *L. rubrilucens, L. sainthelensi, L. sainthelensi, L. shakespearei, L. spiritensis, L. tucsonensis, L. steigerwaltii, L. worsleiensis, L. steelei.*

In one embodiment, a *Legionella* is one or more selected from the following species: *L. pneumophila, L. longbeachae, L. feeleii, L. micdadei*, and *L. anisa.*

Said *L. bozemanae* may be from *L. bozemanae* serogroup 1 (SG1) or *L. bozemanae* serogroup 2 (SG2). Said *L. hackeliae* may be from *L. hackeliae* serogroup 1 (SG1) or *L. hackeliae* serogroup 2 (SG2). Said *L. longbeachae* may be from *L. longbeachae* serogroup 1 (SG1) or *L. longbeachae* serogroup 2 (SG2). Said *L. micdadei* may be *L. micdadei tatlock* or *L. micdadei heba.*

In preferable embodiment, the *Legionella* is *Legionella pneumophila*. Said *Legionella pneumophila* may be from one or more of the following strains: SG1, SG6, SG7, SG8, SG9, SG10, SG11, SG12, SG13, SG14, SG15, and SG16.

In one embodiment, the *Legionella* is one or more *Legionella pneumophila* strain (e.g. isolate) selected from: *L. pneumophila* sg1 Pontiac-1, *L. pneumophila* sg1 Benidorm 030E, *L. pneumophila* sg1 OLDA, *L. pneumophila* sg1 Allentown-1, *L. pneumophila* sg1 Bellingham-1, *L. pneumophila* sg1 Knoxville-1, *L. pneumophila* sg1 France 5811, *L. pneumophila* sg1 Oxford 4032E, *L. pneumophila* sg1 Heysham-1, *L. pneumophila* sg6 Chicago-2, *L. pneumophila* sg7 Chicago 8, *L. pneumophila* sg8 Concorde 3, *L. pneumophila* sg9 IN-23-GI-C2, *L. pneumophila* sg10 Leiden-1, *L. pneumophila* sg11 797-PA-H, *L. pneumophila* sg12 570-CO—H, *L. pneumophila* sg13, *L. pneumophila* sg14 1169-MN-H, *L. pneumophila* sg15 Lansing-3, *L. pneumophila* sg16 Jena-1, *L. pneumophila* sg1 Camperdown-1, *L. pneumophila* sg5 Cambridge-2, *L. pneumophila* sg2 Togus-1, *L. pneumophila* sg5 Dallas, *L. pneumophila* sg3 Bloomington-2, *L. pneumophila* sg6 Oxford-1, *L. pneumophila* subsp. *fraseri* sg4 Los Angeles-1, *L. pneumophila* subsp. *pascullei* MICU-B, *L. pneumophila* subsp. *pascullei* U7W, *L. pneumophila* sg1 Cambridge-1 (NCTC 11231), *L. pneumophila* subsp. *pascullei* U8W, *L. pneumophila* sg1 Washington, *L. pneumophila* sg1 Philadelphia-2 (NC TC 11193), *L. pneumophila* sg1 Kingston-1, *L. pneumophila* sg1 W872.

In one embodiment, the *Legionella* is one or more *Legionella pneumophila* strain (e.g. isolate) selected from: NCTC 11233, NCTC 11406, NCTC 11985, NCTC 12179, NCTC 12180, NCTC 12181 and NCTC 12174. For example, the *Legionella* may be one or more *Legionella pneumophila* strain selected from: NCTC 11233 and NCTC 11406.

While elucidating the optimal components for the present invention, the inventor surprising found that a number of alkali metals and alkaline earth metals (particularly as salts) find utility in suppressing and/or treating *Legionella.*

Thus, aspects and embodiments of the present invention are predicated on the surprising discovery that alkaline earth metal cations such as sodium, lithium, rubidium and caesium and alkali metal cations such as magnesium, calcium, beryllium, strontium and barium are inhibitory (e.g. toxic) to *Legionella* growth. Magnesium, beryllium and calcium cations have been found to be particularly inhibitory (e.g. toxic) to *Legionella.*

This technical effect is highly unexpected, as salts comprising said cations have previously been employed as additives to other bacterial culture media as e.g. buffering agents. Furthermore, potassium cations (an alkali metal) are routinely found in traditional BCYE media (e.g. due to pH adjustment) without suppressing growth, making the inhibitory effects of related metals all the more unexpected.

In one embodiment, a charcoal-free solid agar medium of the present invention does not comprise and inhibitory concentration of an alkaline earth metal-containing salt, an alkali metal-containing salt or any combinations thereof. In one embodiment, a charcoal-free solid agar medium of the present invention comprises an alkaline earth metal-containing salt, an alkali metal-containing salt or a combination thereof at a concentration of less than an inhibitory concentration.

An "inhibitory concentration" means a concentration of an alkaline earth metal-containing salt, an alkali metal-containing salt or a combination thereof that inhibits (e.g. suppresses) the growth of a *Legionella* bacterium.

In one embodiment, an "inhibitory concentration" of an alkaline earth metal-containing salt, an alkali metal-containing salt or a combination thereof is 200 millimolar (mM). Thus, a charcoal-free solid agar medium of the present invention may comprise a concentration of less than 200 mM of an alkaline earth metal-containing salt, an alkali metal-containing salt or any combination thereof.

In one embodiment, an alkali metal-containing salt is one or more selected from a sodium-containing salt, a lithium-containing salt and a rubidium-containing salt.

In one embodiment, an alkali metal-containing salt is one or more selected from a lithium-containing salt and a rubidium-containing salt.

In one embodiment, an alkaline earth metal-containing salt is one or more selected from a magnesium-containing salt, a calcium-containing salt, a beryllium-containing salt, a strontium-containing salt and a barium-containing salt.

In one embodiment, an alkaline earth metal-containing salt is one or more selected from a magnesium-containing salt, a calcium-containing salt, a beryllium-containing salt and a strontium containing salt.

In one embodiment, a charcoal-free solid agar medium of the invention comprises less then an inhibitory concentration of an alkali metal and/or alkaline earth metal. In one embodiment, a charcoal-free solid agar medium of the invention comprises less then an inhibitory concentration of an alkali metal-containing salt and/or alkaline earth metal salt.

In one embodiment, an inhibitory concentration of an alkaline earth metal-containing salt is about 175 mM, 150 mM, 125 mM, 100 mM, 75 mM, 50 mM, 25 mM, 10 mM or 3 mM. In one embodiment, an inhibitory concentration of an alkali metal-containing salt is about 175 mM, 150 mM, 125 mM, 100 mM, 75 mM, 50 mM, 25 mM, 10 mM or 3 mM.

In one embodiment, a charcoal-free solid agar medium of the present invention comprises an alkaline earth metal-containing salt and/or a alkali metal-containing salt at a concentration of about 175 mM, 150 mM, 125 mM, 100 mM, 75 mM, 50 mM, 25 mM, 10 mM or 3 mM.

In one embodiment, a charcoal-free solid agar medium of the present invention comprises an alkaline earth metal ion and/or a alkali metal ion at a concentration of about 175 mM, 150 mM, 125 mM, 100 mM, 75 mM, 50 mM, 25 mM, 10 mM or 3 mM.

In a preferable embodiment, said alkali metal-containing salt is one or more selected from a sodium-containing salt, a lithium-containing salt, a rubidium containing salt and a caesium-containing salt.

In a preferable embodiment, said alkaline earth metal-containing salt is one or more selected from a magnesium-containing salt, a calcium-containing salt, a beryllium-containing salt and a strontium containing salt.

In one embodiment, an inhibitory concentration of a sodium-containing salt is about 200 mM, 175 mM, 150 mM, 125 mM, 100 mM, 75 mM, 50 mM, or 25 mM. Preferably, an inhibitory concentration of a sodium-containing salt is about 150 mM.

In one embodiment, an inhibitory concentration of a lithium-containing salt is about 200 mM, 175 mM, 150 mM, 125 mM, 100 mM, 75 mM, 50 mM, 25 mM, 10 mM or 3 mM. Preferably, an inhibitory concentration of a lithium-containing salt is about 75 mM.

In one embodiment, an inhibitory concentration of a rubidium-containing salt is about 200 mM, 175 mM, 150 mM, 125 mM, 100 mM, 75 mM, 50 mM, 25 mM, 10 mM or 3 mM. Preferably, an inhibitory concentration of a rubidium-containing salt is about 150 mM.

In one embodiment, an inhibitory concentration of a caesium-containing salt is about 200 mM, 175 mM, 150 mM, 125 mM, 100 mM, 75 mM, 50 mM, 25 mM, 10 mM or 3 mM. Preferably, an inhibitory concentration of a caesium-containing salt is about 18 mM.

In one embodiment, an inhibitory concentration of a magnesium-containing salt is about 175 mM, 150 mM, 125 mM, 100 mM, 75 mM, 50 mM, or 25 mM. Preferably, an inhibitory concentration of a magnesium-containing salt is about 32 mM.

In one embodiment, an inhibitory concentration of a calcium-containing salt is about 175 mM, 150 mM, 125 mM, 100 mM, 75 mM, 50 mM, 25 mM, 10 mM or 3 mM. Preferably, an inhibitory concentration of a calcium-containing salt is about 9 mM.

In one embodiment, an inhibitory concentration of a beryllium-containing salt is about 175 mM, 150 mM, 125 mM, 100 mM, 75 mM, 50 mM, 25 mM, 10 mM or 3 mM. Preferably, an inhibitory concentration of a beryllium-containing salt is about 4 mM.

In one embodiment, an inhibitory concentration of a strontium-containing salt is about 175 mM, 150 mM, 125 mM, 100 mM, 75 mM, 50 mM, 25 mM, 10 mM or 3 mM. Preferably, an inhibitory concentration of a strontium-containing salt is about 18 mM.

In one embodiment, an inhibitory concentration of a barium-containing salt is about 175 mM, 150 mM, 125 mM, 100 mM, 75 mM, 50 mM, 25 mM, 10 mM or 3 mM. Preferably, an inhibitory concentration of a barium-containing salt is about 4 mM.

In a preferable embodiment, a charcoal-free solid agar medium of the invention comprises: a concentration of a sodium-containing salt of less than about 150 mM, a concentration of a lithium-containing salt of less than about 75 mM, a concentration of a rubidium-containing salt of less than about 150 mM, a concentration of a caesium containing-salt of less than about 18 mM, a concentration of a magnesium-containing salt of less than about 32 mM; a concentration of a calcium-containing salt of less than about 9 mM, a concentration of a beryllium-containing salt of less than about 4 mM, a concentration of a strontium-containing salt of less than about 18 mM, and/or a concentration of a barium containing-salt of less than about 4 mM.

In one embodiment, a charcoal-free solid agar medium of the present invention does not comprise an alkaline earth metal cation and/or an alkali metal cation. Suitably, a charcoal-free solid agar culture medium of the present invention does not comprise an alkaline earth metal-containing salt or an alkali metal-containing salt.

In one embodiment, a charcoal-free solid agar medium of the present invention does not comprise a sodium cation, a lithium cation, a rubidium cation, a magnesium cation, a calcium cation, a beryllium cation, and/or a strontium cation. Suitably, a charcoal-free solid agar medium of the present invention does not comprise a sodium-containing salt, a lithium-containing salt, a rubidium containing salt, a magnesium-containing salt, a calcium-containing salt, a beryllium-containing salt, a strontium containing salt, or a combination thereof.

In one embodiment, a charcoal-free solid agar medium of the present invention does not comprise a sodium cation, a magnesium cation, and/or a calcium cation. Suitably, a culture medium of the present invention does not comprise a sodium-containing salt, a magnesium-containing salt, and/or a calcium-containing salt.

By exposing *Legionella* to intolerable concentrations of these cations and/or salts, the present inventors have developed methods for suppressing the growth of *Legionella* and corresponding uses of these cations and/or salts e.g. as a disinfectant and therapy.

Another aspect of the invention provides a method for suppressing the growth of a *Legionella* bacterium, said method comprising applying an alkali metal-containing salt and/or an alkaline earth metal-containing salt at a site comprising a *Legionella* bacterium, a site suspected of comprising a *Legionella* bacterium, or a site at risk or comprising a *Legionella* bacterium, wherein:

a) said alkali metal-containing salt is one or more selected from a sodium-containing salt, a lithium-containing salt, a rubidium-containing salt and a caesium-containing salt; and b) said alkaline earth metal-containing salt is one or more selected from a magnesium-containing salt, a calcium-containing salt, a beryllium-containing salt, a strontium-containing salt, and a barium-containing salt;

wherein said applying provides a local concentration of said alkali metal-containing salt and/or alkaline earth metal salt at said site of about 1 mM to about 200 mM.

A further aspect provides use of an alkali metal-containing salt and/or an alkaline earth metal-containing salt for suppressing the growth of *Legionella* at a site comprising a *Legionella* bacterium, at a site suspected of comprising *Legionella* bacterium, or at a site at risk or comprising a *Legionella* bacterium, wherein a) said alkali metal-containing salt is one or more selected from a sodium-containing salt, a lithium-containing salt, a rubidium-containing salt and a caesium-containing salt; and b) said alkaline earth metal-containing salt is one or more selected from a magnesium-containing salt, a calcium-containing salt, a beryllium-containing salt, a strontium containing salt, and a barium-containing salt;

wherein said use comprises providing a local concentration of said alkali metal-containing salt and/or alkaline earth metal salt at said site of about 1 mM to about 200 mM.

In one embodiment, said alkali metal-containing salt is one or more selected from a lithium-containing salt, a rubidium-containing salt and a caesium-containing salt. In one embodiment, said alkali metal-containing salt is one or more selected from a sodium-containing salt, a lithium-containing salt, and a rubidium-containing salt. In one embodiment, said alkali metal-containing salt is one or more selected from a lithium-containing salt and a rubidium-containing salt.

In one embodiment, said alkaline earth metal-containing salt is one or more selected from a magnesium-containing salt, a calcium-containing salt, a beryllium-containing salt, and a strontium containing salt. In one embodiment, said alkaline earth metal-containing salt is one or more selected from a magnesium-containing salt and a calcium-containing salt.

The term "suppressing" may mean "inhibiting the growth of" or "killing". The term "inhibits" or "inhibiting" are synonymous with the term "retards the growth of" a *Legionella* bacterium. In one embodiment, an alkaline earth metal-containing salt and/or alkali metal-containing salt of the invention may "kill" a *Legionella* bacterium or be "used to kill" a *Legionella* bacterium. The term "suppressing" also encompasses preventing the growth of *Legionella* (e.g. when applied as a pre-treatment to prevent contamination with *Legionella*).

This application of a sodium-containing salt, a lithium-containing salt, a rubidium-containing salt, a calcium-containing salt, a beryllium-containing salt and/or a strontium containing salt represents a non-toxic method to suppress growth of *Legionella*. Thus, said salts represent an improvement over typical disinfectants (e.g. bleach, chlorine) which are corrosive, poisonous and/or toxic and typically need to be flushed away thoroughly after use. Furthermore, as *Legionella* is generally an aquatic bacterium which thrives in water systems, employing such soluble salts allows for release of sodium, lithium, rubidium, magnesium, calcium, beryllium and/or strontium cations in water, which allows for targeting of aquatic *Legionella*. Magnesium-containing salts (e.g. magnesium sulphate) is currently used to treat asthma attacks (either via nebuliser or via intravenous injection) representing their safe use as a medicament. Calcium supplements are regularly ingested, and or course sodium-containing salts include table salt. Furthermore, the present inventors have demonstrated that the salts of the present invention have a high $LD_{50}$, further exemplifying their suitability for administration to a subject (see Example 5).

In one embodiment, said "applying" step comprises applying an alkali metal-containing salt and/or alkaline earth metal-containing salt of the invention to a water system. Thus, in one embodiment said site is water. In one embodiment, the site to which an alkali metal-containing salt and/or alkaline earth metal-containing salt of the invention is applied is one or more site selected from a cooling tower, a swimming pool, a domestic water system, a shower, an ice-making machine, a refrigerated cabinet, a spa, a hot spring, or a fountain. A site may comprise water selected from drinking water, swimming pool water, fountain water, spa water, sewage water, water in a pipe, and/or water in a robotics system.

In a preferable embodiment said site is a water heater. Said water heater may be a commercial water heater or a domestic water heater.

In one embodiment, the site to which an alkali metal-containing salt and/or alkaline earth metal-containing salt of the invention is applied comprises or consists of medical equipment, bedding, furniture, walls, or floors such as or floors in a hospital.

In a preferable embodiment, an alkali metal-containing salt and/or alkaline earth metal-containing salt of the invention is applied to water.

An alkali metal-containing salt and/or alkaline earth metal-containing salt may be used at a variety of concentrations in methods and uses of the present invention to suppress the growth of a *Legionella* bacterium.

Preferably, concentrations are used which are generally tolerable (e.g. to humans and or equipment) within the site to which they are applied, and thus do not need to be subsequently diluted/washed away. This is particularly advantageous when a cation/salt of the invention is used to treat water, as the resulting concentration of salt/cation does not adversely affect the usability (e.g. in swimming pools) or drinkability (e.g. as fresh drinking water) of water. For example, the concentrations of salts used typically result in concentrations of alkali metal and/or alkaline earth metal cations in drinking water similar to concentrations found in natural sources.

This is highly advantageous, as no vaccine for *Legionella* is currently available and thus the maintenance of water systems to suppress *Legionella* is crucial to public safety.

In one embodiment, said applying step or use comprises providing a local concentration of said alkali metal-containing salt and/or alkaline earth metal salt at said site (e.g. water) to about 1 mM to about 500 mM, about 1 mM to about 400 mM, about 1 mM to about 300 mM, about 1 mM to about 200 mM, about 1 mM to about 100 mM, about 1 mM to about 50 mM, or about 1 mM to about 10 mM.

In one embodiment, said applying step or use comprises providing a local concentration of said alkali metal-containing salt and/or alkaline earth metal salt at said site to about 1 mM to about 300 mM, about 50 mM to about 250 mM, about 100 mM to about 200 mM. In a preferable embodiment, said applying step or use comprises providing a local concentration of said alkali metal-containing salt and/or alkaline earth metal-containing salt at said site to about 125 mM to about 175 mM.

In one embodiment, said applying step or use comprises providing a local the concentration of said sodium-containing salt at said site to about 1 mM to about 300 mM, about 50 mM to about 250 mM, or about 100 mM to about 200 mM. In a preferable embodiment, said applying step or use comprises providing a local concentration of said sodium-containing salt at said site to about 125 mM to about 175 mM. In a more preferable embodiment, said applying step or use comprises providing a local concentration of said sodium-containing salt at said site to about 150 mM.

In one embodiment, said applying step or use comprises providing a local concentration of said lithium-containing salt at said site to about 1 mM to about 300 mM, about 50 mM to about 250 mM, or about 100 mM to about 200 mM. In a preferable embodiment, said applying step or use comprises providing a local concentration of said lithium-containing salt at said site to about 50 mM to about 100 mM. In a more preferable embodiment, said applying step or use comprises providing a local concentration of said lithium-containing salt at said site to about 75 mM.

In one embodiment, said applying step or use comprises providing a local concentration of said rubidium-containing salt at said site to about 1 mM to about 300 mM, about 50 mM to about 250 mM, or about 100 mM to about 200 mM. In a preferable embodiment, said applying step or use comprises providing a local concentration of said rubidium-containing salt at said site to about 125 mM to about 175 mM. In a more preferable embodiment, said applying step or use comprises providing a local concentration of said rubidium-containing salt at said site to about 150 mM.

In one embodiment, said applying step or use comprises providing a local concentration of said caesium-containing salt at said site to about 1 mM to about 100 mM, about 2 mM to about 50 mM, about 3 mM to about 10 mM, or 4 mM to about 10 mM. In a preferable embodiment, said applying step or use comprises providing a local concentration of said caesium-containing salt at said site to about 5 mM to about 40 mM. In a more preferable embodiment, said applying step or use comprises providing a local concentration of said caesium-containing salt at said site to about 18 mM.

In one embodiment, said applying step or use comprises providing a local concentration of said magnesium-containing salt at said site to about 1 mM to about 200 mM, about 10 mM to about 150 mM, about 20 mM to about 100 mM, or about 30 mM to about 50 mM. In a preferable embodiment, said applying step or use comprises providing a local concentration of said magnesium-containing salt at said site to about 25 mM to about 100 mM. In a more preferable embodiment, said applying step or use comprises providing a local concentration of said magnesium-containing salt at said site to about 40 mM (e.g. 37 mM).

In one embodiment, said applying step or use comprises providing a local concentration of said calcium-containing salt at said site to about 1 mM to about 100 mM, about 2 mM to about 50 mM, about 3 mM to about 10 mM, or about 4 mM to about 10 mM. In a preferable embodiment, said applying step or use comprises providing a local concentration of said calcium-containing salt at said site to about 3 mM to about 20 mM. In a more preferable embodiment, said applying step or use comprises providing a local concentration of said calcium-containing salt at said site to about 9 mM.

In one embodiment, said applying step comprises bringing the concentration of said beryllium-containing salt at said site to about 1 mM to about 100 mM, about 2 mM to about 50 mM, about 3 mM to about 10 mM, or 4 mM to about 10 mM. In a preferable embodiment, said applying step or use comprises providing a local concentration of said beryllium-containing salt at said site to about 1 mM to about 7 mM. In a more preferable embodiment, said applying step or use comprises providing a local concentration of said beryllium-containing salt at said site to about 4 mM.

In one embodiment, said applying step or use comprises providing a local concentration of said strontium-containing salt at said site to about 1 mM to about 100 mM, about 2 mM to about 50 mM, about 3 mM to about 10 mM, or 4 mM to about 10 mM. In a preferable embodiment, said applying step or use comprises providing a local concentration of said strontium-containing salt at said site to about 3 mM to about 20 mM. In a more preferable embodiment, said applying step or use comprises providing a local concentration of said strontium-containing salt at said site to about 18 mM.

In one embodiment, said applying step or use comprises providing a local concentration of said barium-containing salt at said site to about 1 mM to about 100 mM, about 2 mM to about 50 mM, about 3 mM to about 10 mM, or 4 mM to about 10 mM. In a preferable embodiment, said applying step or use comprises providing a local concentration of said barium-containing salt at said site to about 1 mM to about 20 mM. In a more preferable embodiment, said applying step or use comprises providing a local concentration of said barium-containing salt at said site to about 4 mM.

An alkali metal-containing salt and/or an alkaline earth metal-containing salt may be applied together with one or more further chemical suitable for *Legionella* control, such as oxidizing biocides include halogens such as chlorine, bromine, chlorine dioxide, sodium hypochlorite, bromine chloride and non-oxidizing type biocides include organic compounds such as BNPD (2-bromo-2-nitropropane-1, 3-diol), glutaraldehyde, dithiocarbamates, isothiazolin, DBNPA (di-bromo-nitrilo-propionamide), and quaternary ammonium compounds.

Furthermore, an alkali metal-containing salt and/or an alkaline earth metal-containing salt of the invention may be utilised in therapy to treat an infection with *Legionella*. Thus, alkali metal-containing salt and/or an alkaline earth metal-containing salt may be used as a treatment and/or prophylactic for Legionnaires disease.

Thus, another aspect of the invention provides an alkali metal-containing salt and/or an alkaline earth metal-containing salt for use in a method of treating an infection with *Legionella*, wherein a) said alkali metal-containing salt is one or more selected from a sodium-containing salt, a lithium-containing salt, a rubidium containing salt and a caesium-containing salt; and b) said alkaline earth metal-containing salt is one or more selected from a magnesium-containing salt, a calcium-containing salt, a beryllium-containing salt, a strontium containing salt and a barium-containing salt;

wherein said method comprises administering said alkali metal-containing salt and/or said alkaline earth metal-containing salt to a subject by one or more selected from nebulisation, a metered-dose inhaler, intravenously, or any combination thereof.

In one embodiment, said alkali metal-containing salt is one or more selected from a sodium-containing salt, a lithium-containing salt and a rubidium containing salt. In one embodiment, said alkali metal-containing salt is one or more selected from a lithium-containing salt, a rubidium containing salt and a caesium-containing salt. Suitably, said alkali metal-containing salt is one or more selected from a lithium-containing salt and a rubidium containing salt.

In one embodiment, said an alkaline earth metal-containing salt is one or more selected from a magnesium-containing salt, a calcium-containing salt, a beryllium-containing salt and a strontium containing salt. In one embodiment, said alkaline earth metal-containing salt is one or more selected from a magnesium-containing salt, a calcium-containing salt, and a strontium containing salt. Suitably, said alkaline earth metal-containing salt is one or more selected from a magnesium-containing salt, and a calcium-containing salt.

In a preferable embodiment an alkali metal-containing salt and/or alkaline earth metal-containing salt is administered by nebulisation.

"Nebulisation" is a method of administering a substance, for example therapeutic. Nebulisation involves converting a substance (e.g. therapeutic) or solution into an aerosol, which is inhaled directly into the lungs. Advantageously, nebulisation allows administration of a substance in the form of breathable particle to allow fast efficient administration to the lungs, and other organs/tissues of the respiratory pathway (e.g. nose, mouth, pharynx, larynx, trachea, bronchi, and bronchioles).

Thus, in one embodiment an alkali metal-containing salt and/or alkaline earth metal-containing salt is typically administered by means of a nebulisation device (e.g. a nebuliser). Suitable nebulisation devices may include a breath-activated nebuliser (e.g. the AeroEclipse available from Trudell Medical International), a breath-enhanced nebuliser (e.g. Adaptive aerosol delivery (iNeb), available from Philips Respironics; or the AKITA Jet available from Vectura Group plc), a vibrating-mesh nebuliser (Aeroneb Go, Pro available from Aerogen; MicroAir available from Omron; eFlow available from Pari; TouchSpray available from ODEM), or The Aerosol Hood ("Child Hood") from Baby's Breath.

In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6%. In one embodiment an alkali metal-containing salt and/or alkaline earth metal-containing salt is administered by nebulisation with a composition comprising an alkali metal-containing salt and/or alkaline earth metal-containing salt with a gas (oxygen) flow rate of about 1-20 L/min, 2-18 L/min, 4-16 L/min, 6-14 L/min, or 8-12 L/min.

In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6% with a gas (oxygen) flow rate of about 1-20 L/min. In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6% with a gas (oxygen) flow rate of about 2-18 L/min.

In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6% with a gas (oxygen) flow rate of about 4-16 L/min. In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6% with a gas (oxygen) flow rate of about 6-14 L/min. In one embodiment, an alkali metal-containing salt and/or alkaline earth metal-containing salt is administered by nebulisation with a composition comprising an alkali metal-containing salt and/or alkaline earth metal-containing salt at 1-10%, 2-8%, or 4-6% with a gas (oxygen) flow rate of about 8-12 L/min.

In one embodiment, an alkali metal-containing salt and/or alkaline earth metal-containing salt is administered by means of a metered-dose inhaler. Metered-dose inhalers may include inhaler (e.g. aerosol) devices of the kind typically used by an asthma patient to inhale a substance (such as a bronchodilator). One such example of a suitable metered-dose inhaler is the Respimat Soft Mist inhaler from Boehringer Ingelheim.

In one embodiment, an alkali metal-containing salt and/or alkaline earth metal-containing salt is administered by means of a high-flow nasal cannula delivery.

In one embodiment an alkali metal-containing salt and/or alkaline earth metal-containing salt is administered intravenously, e.g. by intravenous injection. A suitable dose may be expressed as gram (g) or milligram (mg) of alkali metal-containing salt and/or alkaline earth metal-containing salt per kilogram (kg) of body weight of a subject receiving the administration. In one embodiment an alkali metal-containing salt and/or alkaline earth metal-containing salt may be intravenously administered at a dose of about 5 mg/kg, 15 mg/kg, 20 mg/kg, 35 mg/kg, 50 mg/kg, 65 mg/kg, 80 mg/kg or 95 mg/kg. Suitably, an alkali metal-containing salt and/or alkaline earth metal-containing salt may be administered a dose of about 40 mg/kg. Said doses are particularly suitable for children.

In one embodiment an alkali metal-containing salt and/or alkaline earth metal-containing salt may be intravenously administered at a dose of about 0.1 g/kg, 0.2 g/kg, 0.4 g/kg, 0.6 g/kg, 0.8 g/kg, 1 g/kg, 1.2 g/kg, 1.4 g/kg, 1.6 g/kg, 1.8 g/kg, 2 g/kg, 2.2 g/kg, 2.4 g/kg, 2.6 g/kg, 2.8 g/kg or 3 g/kg. In one embodiment an alkali metal-containing salt and/or alkaline earth metal-containing salt may be intravenously administered at a dose of about 2 g/kg. Said doses are particularly suitable for adults.

In one embodiment, said alkali metal-containing salt and/or alkaline earth metal-containing salt is comprised within a composition (e.g. for administration). Said composition may be solid, liquid or vaporised composition. Suitably, said composition is a vaporised composition providing means to administer a composition of the invention by inhalation and/or nebulisation.

In one embodiment, a composition comprises a sodium-containing salt at a concentration of at least about 50 mM, 100 mM, 150 mM, 200 mM, 250 mM, 300 mM, 350 mM, or 400 mM. In a preferable embodiment, a composition comprises a sodium-containing salt at a concentration of at least about 150 mM.

In one embodiment, a composition comprises a lithium-containing salt at a concentration of at least about 20 mM, 50 mM, 100 mM, 150 mM, 200 mM, 250 mM, 300 mM, 350 mM, or 400 mM. In a preferable embodiment, a composition comprises a lithium-containing salt at a concentration of at least about 75 mM.

In one embodiment, a composition comprises a rubidium-containing salt at a concentration of at least about 50 mM, 100 mM, 150 mM, 200 mM, 250 mM, 300 mM, 350 mM, or 400 mM. In a preferable embodiment, a composition comprises a rubidium-containing salt at a concentration of at least about 150 mM.

In one embodiment, a composition comprises a caesium-containing salt at a concentration of at least about 5 mM, 10 mM, 25 mM, 50 mM, 100 mM, 150 mM, 200 mM, 250 mM, 300 mM, 350 mM, or 400 mM. In a preferable embodiment, a composition comprises a caesium-containing salt at a concentration of at least about 15 mM.

In one embodiment, a composition comprises a magnesium-containing salt at a concentration of at least about 5 mM, 10 mM, 50 mM, 100 mM, 150 mM, 200 mM, 250 mM, 300 mM, 350 mM, or 400 mM. In a preferable embodiment, a composition comprises a magnesium-containing salt at a concentration of at least about 30 mM (e.g. at least about 32 mM).

In one embodiment, a composition comprises a beryllium-containing salt at a concentration of at least about 1 mM, 2 mM, 4 mM, 5 mM, 10 mM, 50 mM, 100 mM, 150 mM, 200 mM, 250 mM, 300 mM, 350 mM, or 400 mM. In a preferable embodiment, a composition comprises a beryllium-containing salt at a concentration of at least about 4 mM.

In one embodiment, a composition comprises a calcium-containing salt at a concentration of at least about 1 mM, 2 mM, 4 mM, 5 mM, 10 mM, 50 mM, 100 mM, 150 mM, 200 mM, 250 mM, 300 mM, 350 mM, or 400 mM. In a preferable embodiment, a composition comprises a calcium-containing salt at a concentration of at least about 9 mM.

In one embodiment, a composition comprises a strontium-containing salt at a concentration of at least about 1 mM, 2 mM, 4 mM, 5 mM, 10 mM, 50 mM, 100 mM, 150 mM, 200 mM, 250 mM, 300 mM, 350 mM, or 400 mM. In a preferable embodiment, a composition comprises a strontium-containing salt at a concentration of at least about 18 mM.

In one embodiment, a composition comprises a barium-containing salt at a concentration of at least about 1 mM, 2 mM, 4 mM, 5 mM, 10 mM, 50 mM, 100 mM, 150 mM, 200 mM, 250 mM, 300 mM, 350 mM, or 400 mM. In a preferable embodiment, a composition comprises a barium-containing salt at a concentration of at least about 2 mM.

This provides an advantageous alternative to using existing antibiotics, reducing the risk of the development of antibiotic resistance not only in *Legionella* but also in other bacteria. Thus, the present invention provides a therapy for treating *Legionella* which is simple to administer and can be readily incorporated into existing therapies.

In one embodiment, an alkali metal-containing salt and/or an alkaline earth metal-containing salt is administered together with a pharmaceutically acceptable carrier.

In one embodiment, an alkaline earth metal-containing salt and/or an alkaline earth metal-containing salt is administered orally, for example together with a foodstuff.

Advantageously, an alkali metal-containing salt and/or alkaline earth metal-containing salt of the invention may be administered at the same time as administering (e.g. either concomitantly or in a separate administration step) another antibiotic. Said antibiotic may be one or more selected from fluoroquinolones, azithromycin, or doxycycline. Other antibiotics may also be used.

In one embodiment, a sodium-containing salt is selected from sodium chloride, hepes sodium salt, sodium acetate anhydrous, sodium acetate trihydrate, sodium azide, sodium β-glycerophosphate, sodium benzoate, sodium bicarbonate, sodium bisulphite, sodium borate decahydrate, sodium borohydride, sodium bromide, sodium carbonate anhydrous, sodium carbonate decahydrous, sodium carbonate monohydrous, sodium chlorite, sodium iodide, sodium nitrate, sodium nitrite, sodium silicate, sodium sulfate, sodium sulfite, sodium tripolyphosphate, sodium chloroacetate, sodium chlorate, sodium metabisulfite, or ANY combination thereof.

In one embodiment, a sodium-containing salt is sodium sulfate. In a preferable embodiment, a sodium-containing salt is sodium chloride.

In one embodiment, a magnesium-containing salt is selected from magnesium chloride, hepes magnesium salt, magnesium acetate anhydrous, magnesium acetate trihydrate, magnesium azide, magnesium β-glycerophosphate, magnesium benzoate, magnesium bicarbonate, magnesium bisulphite, magnesium borate decahydrate, magnesium borohydride, magnesium bromide, magnesium carbonate anhydrous, magnesium carbonate decahydrous, magnesium carbonate monohydrous, magnesium chlorite, magnesium iodide, magnesium nitrate, magnesium nitrite, magnesium silicate, magnesium sulfate, magnesium sulfite, magnesium tripolyphosphate, magnesium chloroacetate, magnesium chlorate, magnesium metabisulfite, or any combination thereof.

In one embodiment, a magnesium-containing salt is magnesium sulfate. In a preferable embodiment, a magnesium-containing salt is from magnesium chloride.

In one embodiment, a calcium-containing salt is selected from calcium chloride, hepes calcium salt, calcium acetate anhydrous, calcium acetate trihydrate, calcium azide, calcium β-glycerophosphate, calcium benzoate, calcium bicarbonate, calcium bisulphite, calcium borate decahydrate, calcium borohydride, calcium bromide, calcium carbonate anhydrous, calcium carbonate decahydrous, calcium carbonate monohydrous, calcium chlorite, calcium iodide, calcium nitrate, calcium nitrite, calcium silicate, calcium sulfate, calcium sulfite, calcium tripolyphosphate, calcium chloroacetate, calcium chlorate, calcium metabisulfite, or any combination thereof.

In one embodiment, a calcium-containing salt is calcium sulfate. In a preferable embodiment, a calcium-containing salt is calcium chloride.

In one embodiment, a lithium-containing salt is selected from lithium chloride, lithium sulfate, lithium hydroxide, hepes lithium salt, lithium acetate anhydrous, lithium acetate trihydrate, lithium azide, lithium β-glycerophosphate, lithium benzoate, lithium bicarbonate, lithium bisulphite, lithium borate decahydrate, lithium borohydride, lithium bromide, lithium carbonate, lithium carbonate anhydrous, lithium carbonate decahydrous, lithium carbonate monohydrous, lithium chlorite, lithium iodide, lithium nitrate, lithium nitrite, lithium silicate, lithium sulfite, lithium tripolyphosphate, lithium chloroacetate, lithium chlorate, lithium metabisulfite, or any combination thereof.

In one embodiment, a lithium-containing salt is lithium sulfate. In a preferable embodiment, a lithium-containing salt is lithium chloride.

In one embodiment, a rubidium-containing salt is selected from rubidium chloride, rubidium sulfate, rubidium hydroxide, hepes rubidium salt, rubidium acetate anhydrous, rubidium acetate trihydrate, rubidium azide, rubidium β-glycerophosphate, rubidium benzoate, rubidium carbonate, rubidium bicarbonate, rubidium bisulphite, rubidium borate decahydrate, rubidium borohydride, rubidium bromide, rubidium carbonate anhydrous, rubidium carbonate decahydrous, rubidium carbonate monohydrous, rubidium chlorite, rubidium iodide, rubidium nitrate, rubidium nitrite, rubidium silicate, rubidium sulfite, rubidium tripolyphosphate, rubidium chloroacetate, rubidium chlorate, rubidium metabisulfite, or any combination thereof.

In one embodiment, a rubidium containing-salt is rubidium sulfate. In a preferable embodiment, a rubidium-containing salt is rubidium chloride.

In one embodiment, a caesium-containing salt is selected from caesium chloride, caesium sulfate, caesium hydroxide, hepes caesium salt, caesium acetate anhydrous, caesium acetate trihydrate, caesium azide, caesium β-glycerophosphate, caesium benzoate, caesium carbonate, caesium bicarbonate, caesium bisulphite, caesium borate decahydrate, caesium borohydride, caesium bromide, caesium carbonate anhydrous, caesium carbonate decahydrous, caesium carbonate monohydrous, caesium chlorite, caesium iodide, caesium nitrate, caesium nitrite, caesium silicate, caesium sulfite, caesium tripolyphosphate, caesium chloroacetate, caesium chlorate, caesium metabisulfite, or any combination thereof.

In one embodiment, a caesium containing-salt is caesium sulfate. In a preferable embodiment, a caesium-containing salt is caesium chloride.

In one embodiment, a beryllium-containing salt is selected from beryllium chloride, beryllium sulfate, beryllium hydroxide, hepes beryllium salt, beryllium acetate anhydrous, beryllium acetate trihydrate, beryllium azide, beryllium β-glycerophosphate, beryllium benzoate, beryllium bicarbonate, beryllium bisulphite, beryllium borate decahydrate, beryllium borohydride, beryllium bromide, beryllium carbonate, beryllium carbonate anhydrous, beryllium carbonate decahydrous, beryllium carbonate monohydrous, beryllium chlorite, beryllium iodide, beryllium nitrate, beryllium nitrite, beryllium silicate, beryllium sulfite, beryllium tripolyphosphate, beryllium chloroacetate, beryllium chlorate, beryllium metabisulfite, or any combination thereof.

In one embodiment, a beryllium containing-salt is beryllium sulfate. In a preferable embodiment, a beryllium-containing salt is beryllium chloride.

In one embodiment, a strontium-containing salt is selected from strontium chloride, strontium sulfate, strontium hydroxide, hepes strontium salt, strontium acetate anhydrous, strontium acetate trihydrate, strontium azide, strontium β-glycerophosphate, strontium benzoate, strontium bicarbonate, strontium bisulphite, strontium borate decahydrate, strontium borohydride, strontium bromide, strontium carbonate anhydrous, strontium carbonate, strontium carbonate decahydrous, strontium carbonate monohydrous, strontium chlorite, strontium iodide, strontium nitrate, strontium nitrite, strontium silicate, strontium sulfite, strontium tripolyphosphate, strontium chloroacetate, strontium chlorate, strontium metabisulfite, or any combination thereof.

In one embodiment, a strontium containing-salt is strontium sulfate. In a preferable embodiment, a strontium-containing salt is strontium chloride.

In one embodiment, a barium-containing salt is selected from barium chloride, barium sulfate, barium hydroxide, hepes barium salt, barium acetate anhydrous, barium acetate trihydrate, barium azide, barium β-glycerophosphate, barium benzoate, barium bicarbonate, barium bisulphite, barium borate decahydrate, barium borohydride, barium bromide, barium carbonate anhydrous, barium carbonate, barium carbonate decahydrous, barium carbonate monohydrous, barium chlorite, barium iodide, barium nitrate, barium nitrite, barium silicate, barium sulfite, barium tripolyphosphate, barium chloroacetate, barium chlorate, barium metabisulfite, or any combination thereof.

In one embodiment, a barium containing-salt is barium sulfate. In a preferable embodiment, a barium-containing salt is barium chloride.

Embodiments related to the various methods of the invention are intended to be applied equally to the solid microbiological culture medium, uses thereof/methods comprising the use of the same, and vice versa.

Sequence Identity

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

ALIGNMENT SCORES FOR DETERMINING SEQUENCE IDENTITY

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{\text{[length of the longer sequence plus the number of gaps introduced into the longer sequence in order to align the two sequences]}} \times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethyl homo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, N.Y. (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

Amino acids are referred to herein using the name of the amino acid, the three letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a medium" includes a plurality of such media and reference to "the bacterium" includes reference to one or more bacteria and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

BRIEF DESCRIPTION OF THE DRAWINGS

Embodiments of the invention will now be described, by way of example only, with reference to the following Figures and Examples.

EXAMPLES

Materials & Methods

Culture Medium

Figure 1A:
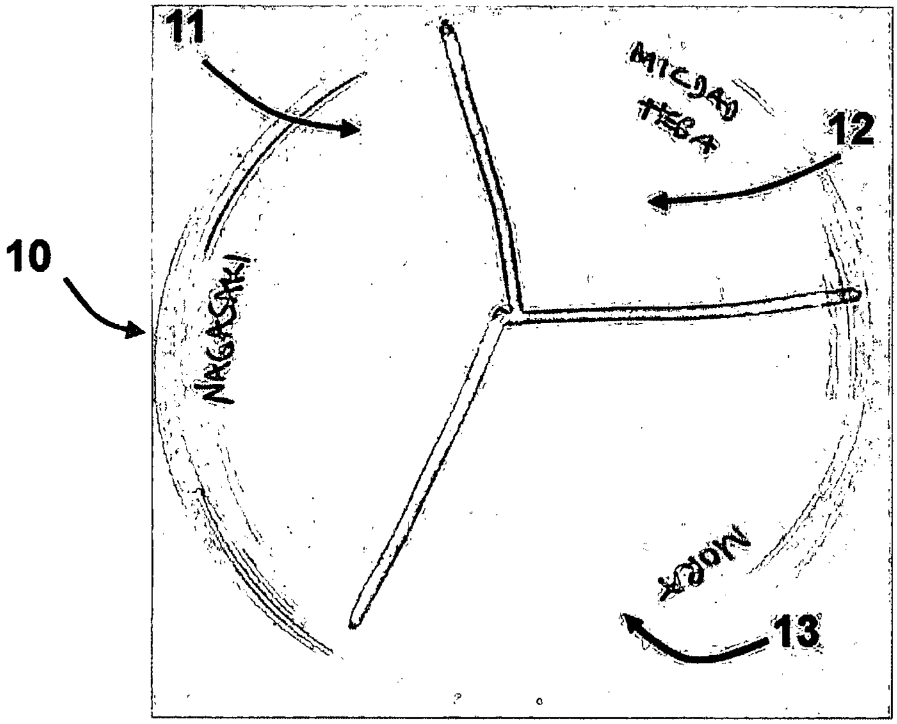
FIGS. 1 (A) and (B) show images of a petri dish with an agar medium of the present invention. Successful growth of various species of *Legionella* can be seen as bacterial streaks, growing in various parts of the agar (separated in three). The plates were incubated for 48 hours at 37° C. after the bacteria were streaked with bacterial culture.

Starting materials for preparing a charcoal-free solid agar medium of the invention were prepared as follows.

The agar was prepared by first dissolving 5 g of select agar (Sigma Aldrich—Cat. No. A5054) in 200 mL deionised water. This was then autoclaved at approximately 121° C. for 15 minutes, and then placed in a water bath at 50° C. until the temperature of the autoclaved agar reached 50° C. 5 g of yeast extract (Sigma Aldrich—Cat. No. 07533), used as the nitrogen source, was then dissolved in deionised water and made up to 200 mL. The culture media typically comprised additional components: a solution of L-cysteine (Sigma Aldrich—Cat. No. W326305) was also made by dissolving 0.4 g of crystal L-cysteine in deionised water and making it up to 10 mL. The yeast extract solution, a 50 mL solution of 20 mM N-(2-Acetamido)-2-aminoethane sulfonic acid (pH 6.9, adjusted with potassium hydroxide), 0.25 g/L ferric pyrophosphate and 1.0 g/L alpha-ketoglutarate and 5 mL of the L-cysteine solution were filter-sterilised using a Corning® 500 mL vacuum filter/storage bottle system with a 0.22 μM pore and placed in a water bath at 50° C. Horse serum used was Gibco Horse serum (heat inactivated, New Zealand origin) from ThermoFisher Scientific, catalogue number 26050088.

The select agar (in melted form, typically 1% agar in $ddH_2O$) was mixed with the other components and poured into agar plates (an allowed to solidify).

A first solid medium was prepared with above mentioned starting materials, and had the following components: 10% (v/v) horse serum, 1% (w/v) yeast extract and 1% (w/v) select agar (pH adjusted to ~6.9 with a sufficient volume of KOH—said percentage values are the % values prior to any dilution due to KOH dilution).

A second solid medium was prepared with the above mentioned starting materials, and had the components outlined in Table 1 (pH adjusted to ~6.9 with a sufficient volume of KOH—said percentage values are the % values prior to any dilution due to KOH dilution). The inventors propose to name this medium (as outlined in Table 1) "Lasarus medium", which stands for *Legionella* antibiotic susceptibility and resistance universal screening medium. This name remains tentative at the time of writing. Thus, reference to the term "Lasarus" or "Lasarus medium" as used herein means the charcoal-free solid agar medium according to Table 1.

A control medium was prepared according to the protocol outlined in Armon and Payment, Journal of Microbiological Methods 11 (1990), pages 65-71 (incorporated herein by reference).

Bacterial Strains

The growth of >35 *Legionella* species has been demonstrated on a solid culture medium of the present invention, including 12 serogroups of *Legionella pneumophila*. Each of said strains are outlined in Tables 2 and 3 below, together with their identification number at The National Collection of Type Cultures (NCTC).

Monitoring Growth of *Legionella*

A petri dish was filled with an agar medium of the present invention (i.e. medium comprising agar), to provide a solid culture medium in the dish. A sterilised loop was typically used to transfer bacteria from a liquid culture of *Legionella* to said agar medium, by dipping the loop in the liquid bacterial culture and subsequently streaking the loop across the surface of the agar medium.

The dishes were then incubated for 48 hours at 37° C. Successful growth of various species of *Legionella* on the agar medium was observed as bacterial streaks.

Example 1 —*Legionella* Species Grown on Culture Medium

The present inventors demonstrated that a *Legionella* pneumophilia isolate can be cultured on a charcoal-free solid agar medium having an agar base with the following ingredients: 10% (v/v) horse serum (Gibco), 1% (w/v) yeast extract and 1% (w/v) select agar.

Table 2 outlines a list of *Legionella* species which the inventors have successfully cultured with a Lasarus (e.g. Table 1) culture medium of the present invention (e.g. on agar plates comprising a medium of the present invention). Each of these species were found to grow at a substantially equivalent level to that achieved on BCYE agar medium.

TABLE 2

| *Legionella* species and serogroup (ag) | Strain identifier | *Legionella* species and serogroup (ag) | Strain identifier |
|---|---|---|---|
| *L. adelaidensis* | NCTC 12735T | *L. gresilensis* | NCTC 13312T |
| *L. anisa* | NCTC 11974T | *L. hackeliae* sg1 | NCTC 11979T |
| *L. beliardensis* | NCTC 13315T | *L. hackeliae* sg2 | NCTC 11980 |
| *L. birminghamensis* | NCTC 12437T | *L. impletisoli* | DSM 18493T |
| *L. bozemanae* sg1 | NCTC 11368T | *L. israelensis* | NCTC 12010T |
| *L. bozemanae* sg2 | NCTC 11975 | *L. jamestowniensis* | NCTC 11981T |
| *L. brunensis* | NCTC 12240T | *L. jordanis* | NCTC 11533T |
| *L. busanensis* | NCTC 13316T | *L. lansingensis* | NCTC 12830T |
| *L. cherrii* | NCTC 11976T | *L. londiniensis* | NCTC 12931 |
| *L. cincinnatiensis* | NCTC 12438T | *L. longbeachae* sg1 | NCTC 11477T |
| *L. donaldonsii* | NCTC 13292 | *L. longbeachae* sg2 | NCTC 11530 |
| *L. dresdeniensis* | NCTC 13409T | *L. maceachernii* | NCTC 11982T |
| *L. dumoffii* | NCTC 11370T | *L. micdadei tatlock* | NCTC 11371T |
| *L. erythra* | NCTC 11977T | *L. micdadei heba* | NCTC 11403 |
| *L. fairfieldensis* | NCTC 12488T | *L. moravica* | NCTC 12239T |
| *L. feeleii* sg1 | NCTC 12022T | *L. nagasakiensis* sp. nov. | ATCC BAA-1558T |
| *L. feeleii* sg2 | NCTC 11978 | *L. taurinensis* | NCTC 13314T |
| *L. geestiana* | NCTC 12373T | *L. wadsworthii* | NCTC 11532T |
| *L. gormanii* | NCTC 11401T | *L. yabuuchiae* | DSM 18492T |
| *L. gratiana* | NCTC 12388T | *L. nautarum* | NCTC 12932T |
| *L. oakridgensis* | NCTC 11531T | *L. parisiensis* | NCTC 11983T |

TABLE 2-continued

| *Legionella* species and serogroup (ag) | Strain identifier | *Legionella* species and serogroup (ag) | Strain identifier |
|---|---|---|---|
| *L. quateirensis* | NCTC 12376T | *L. quinlivanii* sg1 | NCTC 12433T |
| *L. quinlivanii* sg2 | NCTC 12434 | *L. rubrilucens* | NCTC 11987T |
| *L. sainthelensi* sg1 | NCTC 11988T | *L. sainthelensi* sg2 | NCTC 12450 |
| *L. shakespearei* | NCTC 12829T | *L. spiritensis* sg2 | NCTC 12082 |
| *L. tucsonensis* | NCTC 12439T | *L. steigerwaltii* | NCTC 11991T |
| *L. worsleiensis* | NCTC 12377T | *L. steelei* sp. nov. | ATCC BAA-2169T |

NCTC; The National Collection of Type Cultures (Public Health England)

Figure 1B:
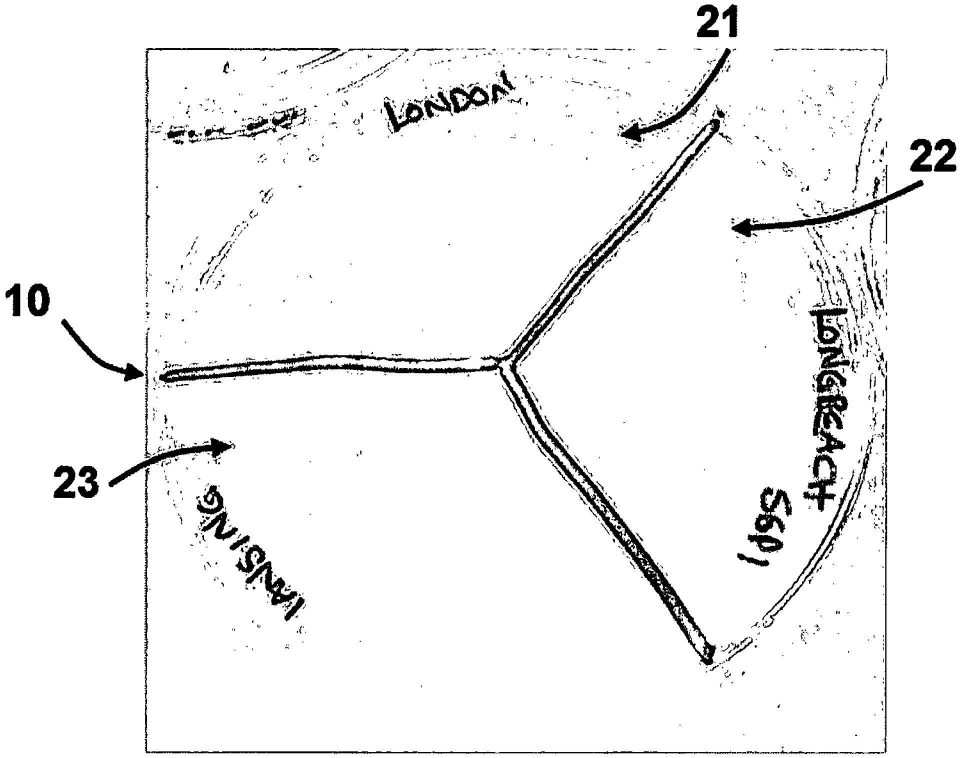

FIG. 1 is provided to demonstrate the successful growth of *L. nagasakiensis* sp. *nov.* (11), *L. micdadei heba* (12), *L. moravica* (13), *L. londiniensis* (21), *L. longbeachae* sg1 (22), and *L. lansingensis* (23) on agar media of the present invention in a petri dish (10). Said bacteria grew readily in dense streaks after being streaked out across the agar medium (e.g. Lasarus medium).

Example 2—*Legionella pneumophila* Strains Grown on Culture Medium

The present inventors have validated the growth of 80 characterised, sequenced *Legionella pneumophila* strains on the culture medium of the present invention, with growth comparable to that on classically prepared BCYE agar medium.

Table 3 outlines a list of exemplified *Legionella pneumophila* strains which the inventors have successfully cultured with a Lasarus culture medium of the present invention (e.g. on agar plates comprising a medium of the present invention).

TABLE 3

| | |
|---|---|
| *L. pneumophila* sg1 Pontiac-1 | *L. pneumophila* sg7 Chicago 8 |
| *L. pneumophila* sg1 Benidorm 030E | *L. pneumophila* sg8 Concorde 3 |
| *L. pneumophila* sg1 OLDA | *L. pneumophila* sg9 IN-23-GI-C2 |
| *L. pneumophila* sg1 Allentown-1 | *L. pneumophila* sg10 Leiden-1 |
| *L. pneumophila* sg1 Bellingham-1 | *L. pneumophila* sg11 797-PA-H |
| *L. pneumophila* sg1 Knoxville-1 | *L. pneumophila* sg12 570-CO-H |
| *L. pneumophila* sg1 France 5811 | *L. pneumophila* sg13 |
| *L. pneumophila* sg1 Oxford 4032E | *L. pneumophila* sg14 1169-MN-H |
| *L. pneumophila* sg1 Heysham-1 | *L. pneumophila* sg15 Lansing-3 |
| *L. pneumophila* sg6 Chicago-2 | *L. pneumophila* sg16 Jena-1 |
| *L. pneumophila* sg1 Camperdown-1 | *L. pneumophila* sg5 Cambridge-2 |
| *L. pneumophila* sg2 Togus-1 | *L. pneumophila* sg5 Dallas |
| *L. pneumophila* sg3 Bloomington-2 | *L. pneumophila* sg6 Oxford-1 |
| *L. pneumophila* subsp. *fraseri* sg4 Los Angeles-1 | L. pneumophila subsp. *pascullei* MICU-B |
| *L. pneumophila* subsp. *pascullei* U7W | *L. pneumophila* sg1 Cambridge-1 (NCTC 11231) |
| *L. pneumophila* subsp. *pascullei* U8W | *L. pneumophila* sg1 Washington |
| *L. pneumophila* sg1 Philadelphia-2 (NCTC 11193) | *L. pneumophila* sg1 Kingston-1 |
| *L. pneumophila* sg1 W872 | |

Example 3—*Legionella pneumophila* Serogroups Grown on Culture Medium

The following list outlines a number of *Legionella pneumophila* strains which the inventors have successfully cultured with a Lasarus culture medium of the present invention (e.g. on agar plates comprising a medium of the present invention): SG1, SG6, SG7, SG8, SG9, SG10, SG11, SG12, SG13, SG14, SG15, and SG16.

Example 4—Comparison with BCYE Agar Medium and BCY Broth

As previously explained, the present inventors have validated the growth of 80 characterised, sequenced *Legionella pneumophila* strains on the Lasarus culture medium of the present invention, with growth comparable to that on classically prepared BCYE agar medium.

However in contrast to BCYE medium, the present inventors have shown that it is possible to perform antimicrobial susceptibility testing on the culture medium of the present invention with a range of antibiotics. The results of susceptibility testing using the present medium were comparable to those that could previously only be performed in microbroth (liquid) culture (Vandewalle-Capo et. al. 2017, International Journal of Antimicrobial Agents, 50 (2017) 684-689). However, the present medium provides a solid culture medium which can be used with an automated multipin inoculator to examine a plurality (e.g. up to at least 80 strains) of *Legionella* at a time for a range of antibiotic concentrations e.g. without need to sterilise the inoculator in between antibiotics. This allows significant scale-up and automation to be utilised. This was also the preferable method by which the MIC50 and MIC90 of alkali metal-containing salt and/or alkaline earth metal-containing salt was determined. The method is readily adaptable for determining the effective ranges (and screen for resistant isolates) for testing decontaminating agents and biocides (including heavy metals and oxidising chemicals).

Example 5—Comparison with Control Medium

The growth of the following *L. pneumophila* strains (all obtained from the National Collection of Type Cultures) on both Lasarus medium and the control medium (described above) were directly compared:

NCTC 11985, NCTC11406, NCTC11233, NCTC12180, NCTC12179, NCTC12181, NCTC 12174.

Colonies of the strain (grown on standard BCYE agar plates) were suspended in sterile water (to provide the suspention), and a series of 2-fold dilutions were prepared. The suspension and each of the dilutions were contacted at defined regions of a plate having Lasarus medium, and a plate having Control Medium i.e. LTM, as described in Armon & Payment (with the suspension on the very left).

Both media were inoculated from the same starting culture, and incubating under identical conditions, e.g. identical temperature, and incubation time etc.

Figure 2:
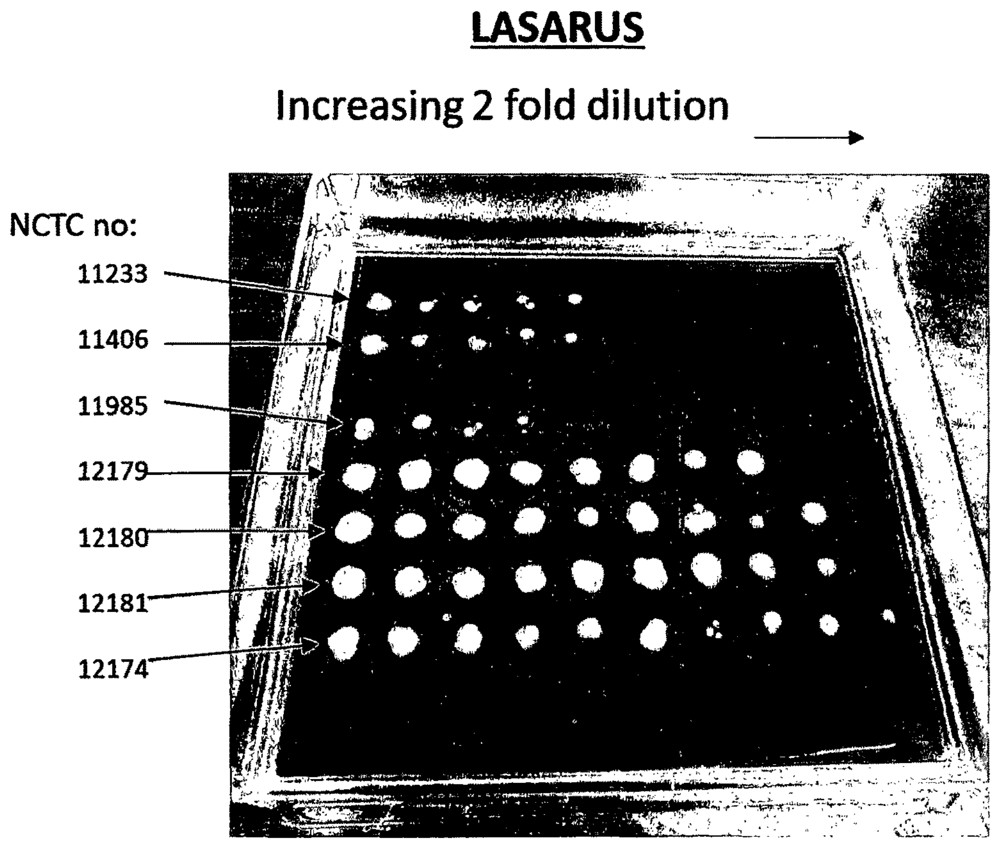
FIG. 2 shows images of a petri dish with an agar medium of the present invention (Lasarus), and a control medium (described in Materials and Methods). Successful growth of each *Legionella* strain tested can be seen as a bacterial load (e.g. bacterial colonies) on Lasarus medium. Improved growth efficiency on Lasarus medium (in comparison with the control medium) is shown.
Figure 2:
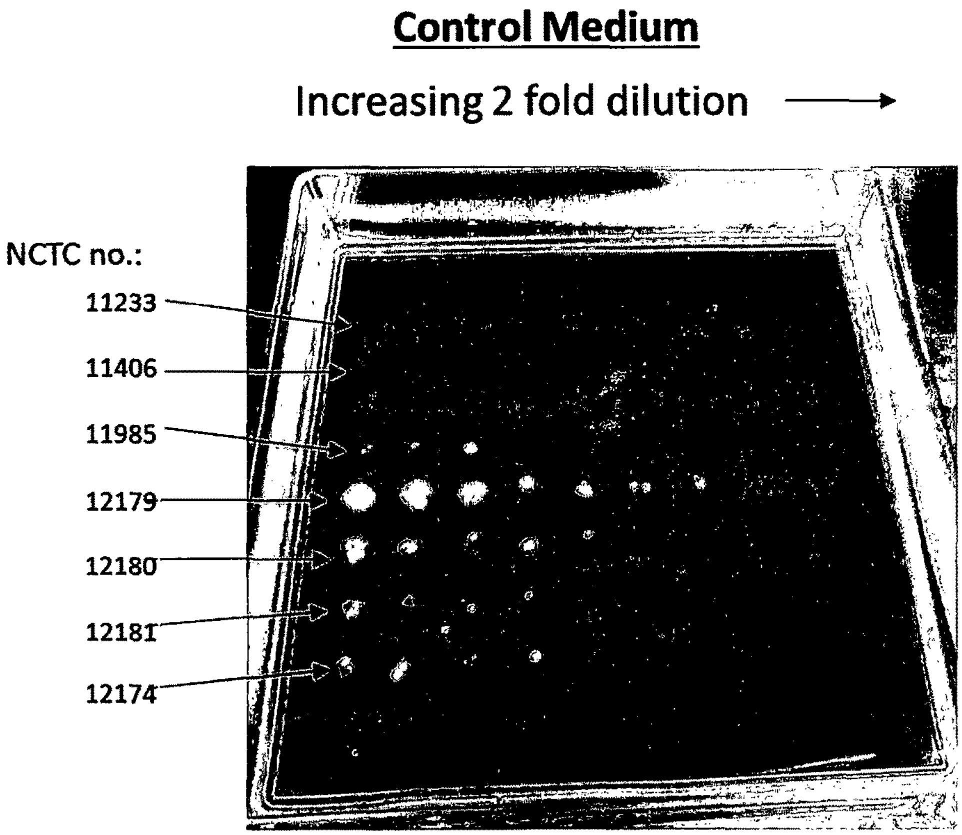

The results show that growth efficiency (for each strain) across each dilution was significantly greater on Lasarus medium compared to the growth medium—see FIG. 2. Furthermore, Lasarus medium supported growth of each tested strain. In comparison, the control medium was not capable of supporting growth of a number of the strains tested (e.g. NCTC 11233 and NCTC 11406).

Example 6—Antibiotic Susceptibility Testing

A total of 92 *Legionella pneumophila* isolates (as described in Wilson et. al., J Antimicrob Chemother. 2018 Jul. 24. doi: 10.1093/jac/dky253, incorporated herein by reference) were tested for antibiotic susceptibility on the solid culture medium (Lasarus). MIC data (calculated by art recognised serial dilution experiments), including average MIC50 across the tested isolates, is presented in Table 4 below.

This demonstrates that *Legionella* retains high susceptibility to these antibiotics (known to suppress *Legionella*) on Lasarus. Such susceptibility is not achievable when *Legionella* is cultured on prior art solid medium (e.g. solid media comprising charcoal, such as BCYE).

TABLE 4

| Antibiotics | Ranges (MIC100) μg/ml | MIC50 μg/ml (average) | MIC90 μg/ml (average) |
|---|---|---|---|
| Ciprofloxacin | 0.008-0.06 | 0.03 | 0.06 |
| Tetracycline | 32-128 | 128 | 128 |
| Azithromycin | 0.008-0.25 | 0.03 | 0.125 |
| Rifampacin | 0.002-0.008 | 0.004 | 0.008 |
| Ampacilin | 1 to 32 | 8 | 32 |
| Gentamycin | 0.06-1 | 0.25 | 0.5 |
| Chloramphenicol | 0.25-1 | 0.5 | 0.5 |
| Levofloxacin | 0.008-0.06 | 0.03 | 0.06 |

Of particular note is the susceptibility to azithromycin. It has previously been reported that azithromycin (amongst other antibiotics) does not perform reliably on prior art solid media capable of supporting *Legionella* growth. For a reliable comparison, the susceptibility (MIC data) of a strain of *Staphylococcus aureus* (ATCC strain 29213—used as the international Quality control strain for API, BBL, bioMerieux Vitek, Micro-Media, MicroScan®, and Sensititre products) was tested on a Lasarus medium of the invention, as well as on standard Mueller-Hinton agar (M-Hinton), which does not have components similar to charcoal which absorb/inhibit such antibiotics (Table 5). It was found that MIC on standard Mueller-Hinton agar for azithromycin (amongst other antibiotics) was identical to medium of the present invention. This demonstrates a good conformity of susceptibility results obtained with the present medium to results obtained in routine antibiotic susceptibility medium.

TABLE 5

| Antibiotic | Range tested (mg/L) | MIC100 μg/ml (on M-Hinton) | MIC100 μg/ml (on Lasarus medium) |
|---|---|---|---|
| Levofloxacin | 0.008-2.0 | 0.25 | 0.25 |
| Azithromycin | 0.5-4.0 | 2 | 2 |
| Rifampacin | 0.004-0.03 | 0.016 | 0.016 |
| Chloramphenicol | 2.0-16.0 | 4 | 4 |

Example 7—Comparison of Antibiotic Susceptibility

Susceptibility of various strains of *L. pneumophila* (when grown on Lasarus, or BCYE agar) to the antibiotics rifampicin, levofloxacin, and azithromycin was tested. Experiments were performed in quadruplicate.

Rifampicin: it was found that ~35 (on average) of the strains tested could grow on Lasarus medium having a rifampicin concentration of 0.004 μg/ml. This number reduced to less than 15 strains (on average) on medium having a rifampicin concentration of 0.004 μg/ml. None of the tested strains could grow on Lasarus medium having a rifampicin concentration of 0.016 μg/ml. In comparison, more than 30 strains (on average) could grow on BCYE having a rifampicin concentration of 0.06 μg/ml, and more than 15 strains (on average) could grow on BCYE having a rifampicin concentration of 0.125 µg/ml.

Levofloxacin: it was found that ~30 (on average) of the strains tested could grow on Lasarus medium having a levofloxacin concentration of 0/03 µg/ml. None of the tested strains could grow on Lasarus medium having a levofloxacin concentration of 0.125 µg/ml. In comparison, more than 25 strains (on average) could grow on BCYE having a levofloxacin concentration of 1 µg/ml, and more than 15 strains (on average) could grow on BCYE having a levofloxacin concentration of 2 µg/ml.

Azithromycin: it was found that ~20 (on average) of the strains tested could grow on Lasarus medium having an azithromycin concentration of 0.03 µg/ml. This number reduced to less than 15 strains (on average) on medium having an azithromycin concentration of 0.06 µg/ml. None of the tested strains could grow on Lasarus medium having an azithromycin concentration of 0.125 µg/ml. In comparison, more than 20 strains (on average) could grow on BCYE having an azithromycin concentration of 0.25 µg/ml, and more than ~5 strains (on average) could grow on BCYE having an azithromycin concentration of 0.5 µg/ml. The data demonstrates the low activity of antibiotics on BCYE (due to charcoal), which does not occur Lasarus medium (in which the antibiotics retain activity). The data supports the use of Lasarus medium for antibiotic screening.

Example 8—Suppressing Growth of *Legionella* with Alkali Metal-Containing Salts and Alkaline Earth Metal-Containing Salts A series of plates comprising a culture medium of the present invention (e.g. as per Table 1 above) were prepared, with the culture medium in said plates further comprising an alkali metal-containing salt or alkaline earth metal-containing salt at varying concentrations (e.g. typically ranging from about 1 mM to about 250 mM).

The plates were inoculated with *Legionella*, typically with a multi-pin inoculator allowing inoculation in a high-throughput manner. The plates were typically incubated for about 24 h at 37° C.

Bacterial growth was then observed on each of the plates having varying concentrations of an alkali metal-containing salt or alkaline earth metal-containing salt. This allowed determination of the minimum inhibitory concentration 50% (MIC50) and the minimum inhibitory concentration 90% (MIC50) of said salts. This experiment was performed with 74 different isolates of *Legionella*, and the average MIC50 and MIC90 of exemplified salts is outlined in Table 5 below.

Furthermore, the inventors investigated the lethal dose 50% (LD50) of these salts in rats following oral administration. LD50 data is also provided in the table below, provided in mg/kg (mg of salt per kg of rat body weight).

KCl was a very poor suppressor (e.g. it was not a suppressor) of *Legionella* having high (>150 mM, actual value higher than the range tested) MIC90 values.

TABLE 6

| | Compound | MIC50 (mM) | MIC90 (mM) | LD50 (mg/kg) |
|---|---|---|---|---|
| alkali metal-containing salt | LiCl | 75 | 75 | 526 |
| | NaCl | 150 | 150 | 3000 |
| | KCl | >150 | >150 | 2600 |
| | RbCl | 150 | 150 | 4440 |
| | CsCl | 18 | 37 | 2600 |
| alkaline earth metal-containing salt | $BeSO_4$ | 4 | 4 | 82 |
| | MgCl | 37 | 75 | 2800 |
| | $CaCl_2$ | 9 | 18 | 1000 |
| | SrCl | 18 | 18 | 2250 |
| | $BaCl_2$ | 4 | 9 | 78 |

Example 9—Suppressing Growth of *Legionella* in a Subject with Alkali Metal-Containing Salts and Alkaline Earth Metal-Containing Salts A patient presents at a clinic with a *Legionella* infection in their lungs.

An alkali metal-containing salt and/or alkaline earth metal-containing salt of the present invention is administered to the subject by nebulisation, at an appropriate dosage (e.g. with a composition comprising an alkali metal-containing salt and/or alkaline earth metal-containing salt at 1-10%, 2-8%, or 4-6% and at a gas (oxygen) flow rate of about 1-20 L/min, 2-18 L/min, 4-16 L/min, 6-14 L/min, or 8-12 L/min).

A test sample (e.g. sputum) is obtained from the lung of the subject following said treatment, and the bacterial load of *Legionella* (e.g. quantified as colony forming units) in said sample is compared to the bacterial load of *Legionella* in a control sample taken from the subject prior to treatment.

The bacterial load in the test sample is found to be lower than the bacterial load in the control sample, demonstrating that the administration of said alkali metal-containing salt and/or alkaline earth metal-containing salt is suitable for treating a *Legionella* infection.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. An in vitro method for culturing a *Legionella* bacterium, comprising incubating a *Legionella* bacterium on a charcoal-free solid agar medium comprising:
- a) serum, wherein the serum is present at a concentration of 1%-35% (v/v);
- b) a nitrogen source; and
- c) an iron source.

2. A screening method for identifying an antibiotic suitable for suppressing the growth of a *Legionella* bacterium, comprising:
- a. contacting a *Legionella* bacterium with a charcoal-free solid agar medium to provide a test sample, wherein the charcoal-free solid agar medium comprises:
  - i. serum, wherein the serum is present at a concentration of 1%-35% (v/v);
  - ii. a nitrogen source; and
  - iii. an iron source;
- b. incubating the test sample in the presence of a candidate antibiotic; and c. identifying said candidate antibiotic as suitable for suppressing the growth of the *Legionella* bacterium when the bacterial load of said *Legionella* bacterium in the test sample subsequent to incubation is lower than a bacterial load of said *Legionella* bacterium in a control sample, wherein the control sample is incubated in the absence of said candidate antibiotic; or d. identifying said candidate antibiotic as unsuitable for suppressing the growth of the *Legionella* bacterium when the bacterial load of said *Legionella* bacterium in the test sample subsequent to incubation is the same as or greater than the bacterial load of said *Legionella* bacterium in a control sample, wherein the control sample is incubated in the absence of said candidate antibiotic.

3. A kit comprising a charcoal-free solid agar medium for culturing a *Legionella* bacterium, and/or reagents for preparing a charcoal-free solid agar medium for culturing the *Legionella* bacterium, wherein:

a. said charcoal-free solid agar medium comprises:
  i. serum, wherein the serum is present at a concentration of 1%-35% (v/v);
  ii. a nitrogen source; and
  iii. an iron source; and/or
b. said reagents comprise:
  i. agar;
  ii. serum;
  iii. a nitrogen source; and
  iv. an iron source; and wherein said kit further comprises instructions for culturing the *Legionella* bacterium on said charcoal-free solid agar medium.

4. The screening method according to claim 2, wherein said method further comprises the step of recording data obtained in step (c) and/or step (d) on a suitable data carrier.

5. The method according to claim 1, wherein said nitrogen source is one or more of yeast extract, beef extract, liver extract, casein hydrolysate, plant cell extract, soy bean extract or any combination thereof.

6. The method according to claim 1, wherein the iron source is an iron chelate and/or ferric pyrophosphate.

7. The method according to claim 1, wherein:

a. the agar is present at a concentration of 0.2%-5% (w/v);
b. the nitrogen source is present at a concentration of 0.2%-10% (w/v); and/or
c. the iron source is present at a concentration of 0.01%-0.1% (w/v).

8. The method according to claim 1, wherein said charcoal-free solid agar medium further comprises one or more agent comprising:

a. a buffer;
b. alpha-ketoglutarate; and/or
c. cysteine.

9. The method according to claim 1, wherein said charcoal-free solid agar medium further comprises one or more agent comprising:

a. a buffer that is present at a concentration of 1 mM-500 mM;
b. alpha-ketoglutarate that is present at a concentration of 0.001%-1% (w/v); and/or
c. cysteine that is present at a concentration of 1%-10% (w/v).

10. The method according to claim 1, wherein said serum is one or more of horse serum, sheep serum, goat serum, bovine serum, fetal bovine serum, calf serum, mouse serum, rat serum, pig serum, guinea pig serum, porcine serum, or rabbit serum.

11. The method according to claim 1, wherein said serum is horse serum.

12. The method according to claim 1, wherein the *Legionella* bacterium is one or more of the following species: *L. adelaidensis, L. anisa, L. beliardensis, L. birminghamensis, L. bozemanae, L. brunensis, L. busanensis, L. cherrii, L. cincinnatiensis, L. donaldonsii, L. dresdeniensis, L. dumoffii, L. erythra, L. fairfieldensis, L. feeleii, L. geestiana, L. gormanii, L. gratiana, L. gresilensis, L. hackeliae sg*1, *L. impletisoli, L. israelensis, L. jamestowniensis, L. jordanis, L. lansingensis, L. londiniensis, L. longbeachae, L. maceachernii, L. micdadei, L. micdadei, L. moravica, L. pneumophila, L. nagasakiensis, L. taurinensis, L. wadsworthii*, or *L. yabuuchiae.*

13. The screening method according to claim 2, wherein said nitrogen source is one or more of yeast extract, beef extract, liver extract, casein hydrolysate, plant cell extract, soy bean extract or any combination thereof.

14. The screening method according to claim 2, wherein the iron source is an iron chelate and/or ferric pyrophosphate.

15. The screening method according to claim 2, wherein:

a. the agar is present at a concentration of 0.2%-5% (w/v);
b. the nitrogen source is present at a concentration of 0.2%-10% (w/v); and/or
c. the iron source is present at a concentration of 0.01%-0.1% (w/v).

16. The screening method according to claim 2, wherein said charcoal-free solid agar medium further comprises one or more agent comprising:

a. a buffer;
b. alpha-ketoglutarate; and/or
c. cysteine.

17. The screening method according to claim 2, wherein said charcoal-free solid agar medium further comprises one or more agent comprising:

a. a buffer that is present at a concentration of 1 mM-500 mM;
b. alpha-ketoglutarate that is present at a concentration of 0.001%-1% (w/v); and/or cysteine that is present at a concentration of 1%-10% (w/v).

18. The screening method according to claim 2, wherein said serum is one or more of horse serum, sheep serum, goat serum, bovine serum, fetal bovine serum, calf serum, mouse serum, rat serum, pig serum, guinea pig serum, porcine serum, or rabbit serum.

19. The screening method according to claim 2, wherein said serum is horse serum.

20. The screening method according to claim 2, wherein the *Legionella* is one or more of the following species: *L. adelaidensis, L. anisa, L. beliardensis, L. birminghamensis, L. bozemanae, L. brunensis, L. busanensis, L. cherrii, L. cincinnatiensis, L. donaldonsii, L. dresdeniensis, L. dumoffii, L. erythra, L. fairfieldensis, L. feeleii, L. geestiana, L. gormanii, L. gratiana, L. gresilensis, L. hackeliae sgl, L. impletisoli, L. israelensis, L. jamestowniensis, L. jordanis, L. lansingensis, L. londiniensis, L. longbeachae, L. maceachernii, L. micdadei, L. micdadei, L. moravica, L. pneumophila, L. nagasakiensis, L. taurinensis, L. wadsworthii*, or *L. yabuuchiae.*

* * * * *